US008992603B2

(12) United States Patent
Dugas et al.

(10) Patent No.: US 8,992,603 B2
(45) Date of Patent: Mar. 31, 2015

(54) COATED DEVICES AND METHOD OF MAKING COATED DEVICES THAT REDUCE SMOOTH MUSCLE CELL PROLIFERATION AND PLATELET ACTIVITY

(71) Applicants: Nanocopoeia, Inc., St. Paul, MN (US); Louisiana State University Health Sciences Center Office of Research, Shreveport, LA (US)

(72) Inventors: Tammy R. Dugas, Bossier City, LA (US); Alok Khandelwal, Shreveport, LA (US); James John Kleinedler, Shreveport, LA (US); John Devlin Foley, Lino Lakes, MN (US)

(73) Assignees: Nanocopoeia, Inc., St. Paul, MO (US); Louisiana State University Health Sciences Center Office of Research, Shreveport, LA (US)

( * ) Notice: Subject to any disclaimer, the term of this patent is extended or adjusted under 35 U.S.C. 154(b) by 0 days.

(21) Appl. No.: 13/633,578

(22) Filed: Oct. 2, 2012

(65) Prior Publication Data

US 2013/0030518 A1   Jan. 31, 2013

Related U.S. Application Data

(62) Division of application No. 12/740,890, filed as application No. PCT/US2008/082440 on Nov. 5, 2008.

(60) Provisional application No. 61/001,916, filed on Nov. 5, 2007.

(51) Int. Cl.
*A61F 2/82* (2013.01)
*A61L 31/16* (2006.01)
(Continued)

(52) U.S. Cl.
CPC ............... *A61L 31/16* (2013.01); *A61L 31/10* (2013.01); *A61L 31/146* (2013.01); *A61F 2/915* (2013.01);
(Continued)

(58) Field of Classification Search
USPC ............. 604/890.1, 103.02; 422/243, 22; 606/194; 623/1.11, 1.15, 1.42, 1.46
See application file for complete search history.

(56) References Cited

U.S. PATENT DOCUMENTS 5,163,958 A * 11/1992 Pinchuk ............... 623/23.49
6,258,121 B1    7/2001 Yang et al.
(Continued)

OTHER PUBLICATIONS

Igura et al. Resveratrol and quercetin inhibit angiogenesis in vitro. Cancer Letters 171 (2001) 11-16.*
Venkatraman et al. (Release profiles in drug-eluting stents: Issues and uncertainties, Journal of Controlled Release 120 (2007) 149-160).*
SciFinder Results Search. Keywords: Resveratrol, Quercetin, stent. Search performed Nov. 6, 2014.*
(Continued)

*Primary Examiner* — Bhisma Mehta
*Assistant Examiner* — Matthew A Engel
(74) *Attorney, Agent, or Firm* — Davis & Bujold, PLLC; Michael J. Bujold

(57) ABSTRACT

The present invention relates generally to the maintenance of blow flood using drug eluting stents and/or other coated medical devices to increased length of time of blood flow. Further, the present invention relates to drug-releasing coated devices for reducing smooth muscle cell proliferation and platelet activity to further limit restenosis utilizing resveratrol and quercetin, polyphenols that are linked to the cardioprotection of red wine consumption. The present invention also provides products and methods for treating or preventing atherosclerosis, stenosis, restenosis, smooth muscle cell proliferation, platelet cell activation and other clotting mechanisms, occlusive disease, or other abnormal lumenal cellular proliferation condition in a location within the body of a patient.

16 Claims, 18 Drawing Sheets

(51) Int. Cl.
  *A61L 31/10* (2006.01)
  *A61L 31/14* (2006.01)
  *A61F 2/915* (2013.01)

(52) U.S. Cl.
  CPC ............... *A61F 2002/91508* (2013.01); *A61F 2002/91558* (2013.01); *A61F 2250/0067* (2013.01); *A61L 2300/608* (2013.01); *A61L 2300/416* (2013.01); *A61L 2300/422* (2013.01)
  USPC .. 623/1.42; 623/1.46; 604/890.1; 604/103.02

(56) References Cited

U.S. PATENT DOCUMENTS

| | | | |
|---|---|---|---|
| 7,615,548 B2 * | 11/2009 | Gottlieb et al. | 514/183 |
| 8,029,561 B1 * | 10/2011 | Kopia et al. | 623/1.42 |
| 8,257,305 B2 * | 9/2012 | Speck et al. | 604/103.02 |
| 8,414,526 B2 * | 4/2013 | Wang | 604/103.02 |
| 2002/0146424 A1 * | 10/2002 | Benza et al. | 424/184.1 |
| 2003/0236513 A1 * | 12/2003 | Schwarz et al. | 604/890.1 |
| 2007/0199824 A1 | 8/2007 | Hoerr et al. | |
| 2007/0212387 A1 | 9/2007 | Patravale et al. | |

OTHER PUBLICATIONS

SciFinder Results Search. Keywords: Resveratrol, Quercetin, implant or medical device. Search performed Nov. 6, 2014.*
International Search Report and Written Opinion for PCT/US08/82440 dated Nov. 5, 2008.
Liu et al. Effects of trans-resveratrol on hypertension-induced cardiac hypertrophy using the partially nephrectomized rat model. Clinical and Experimental Pharmacology and Physiology vol. 32, Issue 12, pp. 1049-1054, Dec. 2005.
Sanchez et al. Quercetin downregulates NADPH oxidase, increases eNOS activity and prevents endothelial dysfunction in spontaneously hypertensive rats. Journal of Hypertension 2006, 24:75-84.
Kleinedler JJ, Foley JD, Alexander JS, Roerig SC, Hebert VY, Dugas TR. Synergistic effect of resveratrol and quercetin released from drug-eluting polymer coatings for endovascular devices. J Biomed Mater Res B Appl Biomater. Nov. 2011;99(2):266-75.
Popat R, et al. A phase 2 study of SRT501 (resveratrol) with bortezomib for patients with relapsed and or refractory multiple myeloma. Br J Haematol. Mar. 2013;160(5):714-7.
Venkatraman S, et al. Release profiles in drug-eluting stents: Issues and uncertainties. Journal of Controlled Release 120 (2007) 149-160.

* cited by examiner

Unexpanded stent     Expanded stent

18A.

18B.

COATED DEVICES AND METHOD OF MAKING COATED DEVICES THAT REDUCE SMOOTH MUSCLE CELL PROLIFERATION AND PLATELET ACTIVITY

CROSS-REFERENCE TO RELATED APPLICATION

This application is a divisional of U.S. application Ser. No. 12/740,890 filed on Aug. 25, 2010, which is a continuation under 35 U.S.C. §111(a) of International Application No. PCT/US2008/082440 filed on Nov. 5, 2008 and published in English as WO/2009/061787 on May 14, 2009, which claims the benefit under 35 U.S.C. §119(e) of the filing date of U.S. provisional application Ser. No. 61/001,916 filed Nov. 5, 2007, the disclosures of which applications and publications are incorporated by reference herein.

BACKGROUND OF THE INVENTION

The present invention relates generally to the maintenance of blow flood using drug eluting stents and other medical devices to increase length of time of blood flow. Further, the present invention relates to drug-releasing stents and/or other coated medical devices for reducing smooth muscle cell proliferation and platelet activity to further limit restenosis utilizing resveratrol and quercetin, polyphenols that are linked to the cardioprotection of red wine consumption. The present invention also provides products and methods for treating or preventing atherosclerosis, stenosis, restenosis, smooth muscle cell proliferation, platelet cell activation and other clotting mechanisms, occlusive disease, or other abnormal lumenal cellular proliferation condition in a location within the body of a patient.

DESCRIPTION OF RELATED ART

Atherosclerosis is a disease characterized by cholesterol-laden plaque formation within the artery wall, leading to vessel narrowing and blood flow reduction. Occlusion of certain key arteries can precipitate a major cardiac event. In the United States, the prevalence rate of atherosclerosis is predicted to be 1 in 58 or 1.70%. Furthermore, atherosclerosis is the first-listed diagnosis for 35 of every 10,000 hospitalizations in the United States, or 0.35%. Over 70% of patients with atherosclerosis receive some sort of treatment that involves catheritization to correct the blockage. The first such treatment using mechanical opening of the occluded areas relied solely on balloon angioplasty. In this procedure, an inflatable device is inserted through an artery to the blockage via a catheter, at which point the balloon is inflated to create an opening in the stenotic area. One approach to clearing an artery that has been constricted or clogged due to stenosis is percutaneous transluminal coronary angioplasty (PTCA) or balloon coronary angioplasty. In this procedure, a balloon catheter is inserted and expanded in the constricted portion of the vessel for clearing the blockage. About one-third of patients who undergo PTCA suffer from restenosis, the renarrowing of the widened segment, within about six months of the procedure. Restenosed arteries may have to undergo another angioplasty.

The limitation of balloon angioplasty is that it is often only a short-term solution, as both the balloon inflation and stretching of the vessel can denude the vessel wall of endothelium and impart endothelial injury and dysfunction to the surrounding areas. Platelets, lymphocytes and monocytes are then recruited to the injured area. Release of basic fibroblast growth factor (bFGF) and platelet derived growth factor (PDGF) from platelets and dying vascular smooth muscle cells and endothelial cells promotes vascular smooth muscle cells to migrate from the underlying medial layer to the intima, where they begin proliferating. This vascular smooth muscle cell (VSMC) proliferative response induces a re-narrowing of the lumen (or "restenosis"), once again restricting blood flow.

Balloon angioplasty has a restenosis rate of approximately 30% over 6 months and a high rate of coronary artery dissection. The high failure rate of balloon angioplasty led to the use of bare metal stents to improve blood flow. Bare metal stents have been used for the long term maintenance of blow flood and prevention of restenosis. These stents generally consist of expandable metal struts. They are delivered in an unexpanded form to the affected area via a catheter and inner balloon. Once at the site of injury, the balloon is inflated such that the stent is locked in an expanded state. The balloon is then deflated, and the catheter and balloon are removed while the stent remains in place. Bare metal stents have a lowered rate of restenosis in some cases, but failure has still varied between 10%-40%.

Stents are not 100% effective in preventing restenosis at the implant site. Restenosis can occur over the length of the stent and/or past the ends of the stent. Physicians have recently employed new types of stents that are coated with a thin polymer film loaded with a drug that inhibits smooth cell proliferation. These drug-eluting stents (DES) were conceived as a way of further limiting restenosis. In this technology, a coating of some chemical compound is placed on the stent in such a manner that it is released slowly over the course of several months.

The coating is applied to the stent prior to insertion into the artery using methods well known in the art, such as a solvent evaporation technique. The solvent evaporation technique entails mixing the polymer and drug in a solvent. The solution comprising polymer, drug, and solvent can then be applied to the surface of the stent by either dipping or spraying. The stent is then subjected to a drying process, during which the solvent is evaporated, and the polymeric material, with the drug dispersed therein, forms a thin film layer on the stent.

The release mechanism of the drug from the polymeric materials depends on the nature of the polymeric material and the drug to be incorporated. The drug diffuses through the polymer to the polymer-fluid interface and then into the fluid. Release can also occur through degradation of the polymeric material. The degradation of the polymeric material can occur through a number of mechanisms such as hydrolysis or enzymatic cleavage. The degradation can occur via surface erosion or simultaneously throughout the bulk of the polymer film. Degradation adds another dimension to the timing and control drug release profiles in addition to diffusion. In addition, polymer degradation insures that large polymer chains that might elicit foreign body reactions are not left behind.

An important consideration in using coated stents is the release rate of the drug from the coating. It is desirable that an effective therapeutic amount of the drug be released from the stent for the longest period of time possible. Burst release, a high release rate immediately following implantation, is undesirable and a persistent problem. While typically not harmful to the patient, a burst release "wastes" the limited supply of the drug by releasing several times the effective amount required and shortens the duration of the release period. Several techniques have been developed in an attempt to reduce burst release. For example, U.S. Pat. No. 6,258,121 to Yang et al. discloses a method of altering the release rate by blending two polymers with differing release rates and incorporating them into a single layer.

Though this generation of DES holds promise, the currently approved drugs have unfavorable side effects such as the inhibition the formation of a functional vascular endothelium. This can cause potentially life threatening late terms events. Thus, there remains a need for an improved system and method that increases blood flow through stenotic areas and reduces restenosis without side effects from the drugs coating the device. In view of the foregoing, the development of a device having a coating of polymeric material with improved biologically active agent or agents dispersed therein would be a significant advance in the art. The current invention treats and/or prevents atherosclerosis, stenosis, restenosis, smooth muscle cell proliferation, platelet cell activation and other clotting mechanisms, occlusive disease, or other abnormal lumenal cellular proliferation condition in a location within the body of a patient, and can be effective in delivering a wide range of other therapeutic agents to the implant site over a relatively extended period of time.

All references cited herein are incorporated herein by reference in their entireties.

BRIEF SUMMARY OF THE INVENTION

The invention provides a drug eluting intravascular stent comprising: (a) a generally cylindrical stent body; (b) an adherent layer on the stent comprising a composite of polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer. The invention further provides a stent wherein the stent body has a metal surface. The invention further provides a stent wherein the stent body is micro- or nanoporous. The invention further provides a stent wherein the stent body has a polymeric surface. The invention further provides a stent wherein the polymer is a bioabsorbable polymer. The invention further provides a stent wherein the polymer is a biostable polymer. The invention further provides a stent wherein the first and second active agents are in a ratio which is selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a stent wherein the first and second active agents are in a ratio which is selected from the group consisting of about 1:5, about 1:2, and about 1:1 by weight percent.

The invention provides a drug eluting intravascular stent comprising: (a) a generally cylindrical stent body; (b) an adherent layer on the stent comprising a composite of polymer and at least one active agent dispersed within the polymer, wherein the at least one active agent is selected from the group consisting of resveratrol, pharmaceutically acceptable salts of resveratrol, pharmaceutically acceptable derivatives of resveratrol, quercetin, pharmaceutically acceptable salts of quercetin, pharmaceutically acceptable derivatives of quercetin, combinations thereof, and mixtures thereof. The invention further provides a stent wherein the coating is a polymer selected from the group consisting of polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly(etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof. The invention further provides a stent wherein the first and second active agents and polymer are in a ratio selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a stent wherein the composite includes a plurality of layers. The invention further provides a stent wherein the ratio of pharmaceutically active agents to polymer is varied in some of the layers. The invention further provides a stent wherein the biologically active agent is selected from agents which treat or prevent atherosclerosis, stenosis, restenosis, smooth muscle cell proliferation, platelet cell activation and other clotting mechanisms, occlusive disease, or other abnormal lumenal cellular proliferation condition within a body of a patient. The invention further provides a stent wherein the concentration of the first active agent based on the surface area of the stent ranges from about 1 to about 5 µg/mm2, and the concentration of the optional second active agent based on the surface area of the stent ranges from about 1 to about 5 µg/mm2. The invention further provides a stent, wherein each of the active agents may have different release profiles. The invention further provides a stent wherein the release profile of the active agents may be selected between rapid and delayed. The invention further provides a stent wherein a rapid profile coating releases an active agent substantially within one to a few hours. The invention further provides a stent wherein a delayed profile coating releases an active agent and/or agents over a period of at least one month, at least two months, at least six months, or at least one year.

The invention provides the use of a drug eluting intravascular stent comprising: (a) a generally cylindrical stent body; and (b) an adherent layer on the stent comprising a composite of polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer in the manufacture of a medicament for the treatment or prevention of atherosclerosis, stenosis, restenosis, smooth muscle cell proliferation, platelet cell activation and other clotting mechanisms, occlusive disease, or other abnormal lumenal cellular proliferation condition in a location within the body of a patient.

The invention further provides a drug eluting intravascular stent comprising: (a) a generally cylindrical stent body; and (b) an adherent layer on the stent comprising a composite of polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer for use in the treatment or prevention of atherosclerosis, stenosis, restenosis, smooth muscle cell proliferation, platelet cell activation and other clotting mechanisms, occlusive disease, or other abnormal lumenal cellular proliferation condition in a location within the body of a patient.

The invention provides a method for treating or preventing atherosclerosis, stenosis, restenosis, smooth muscle cell proliferation, platelet cell activation and other clotting mechanisms, occlusive disease, or other abnormal lumenal cellular proliferation condition in a location within the body of a patient, comprising: implanting a drug eluting intravascular stent comprising: (a) a generally cylindrical stent body; and (b) an adherent layer on the stent comprising a composite of polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer; further wherein the pharmaceutically active agent is locally delivered at the location in a manner that is adapted to substantially treat or prevent the atherosclerosis, stenosis, restenosis, smooth muscle cell proliferation, platelet cell activation and other clotting mechanisms, occlusive disease, or other abnormal lumenal cellular proliferation condition in the patient. The invention further provides a method wherein the polymer is selected from polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly(etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof. The invention further provides a method wherein the ratio of first to second active agents is in a range selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a method wherein, wherein the ratio of first to second active agents is in the range selected from the group consisting of about 1:5, about 1:2, and about 1:1 resveratrol to quercetin by weight percent. The invention further provides a method wherein, wherein the ratio of the first and second active agents to polymer is in a range selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a method wherein the composite includes a plurality of layers. The invention further provides a method wherein the ratio of pharmaceutically active substances to polymer is varied in some of the layers. The invention further provides a method wherein each of the active agents may have different release profiles. The invention further provides a method wherein the release profile of the active agents may be selected between rapid and delayed. The invention further provides a method wherein a rapid profile coating releases an active agent substantially within one to a few hours. The invention further provides a method wherein a delayed profile coating releases an active agent and/or agents over a period of at least one month, at least two months, at least six months, or at least one year.

The invention provides an implantable medical device, comprising: an expandable balloon catheter having an outer surface; and an adherent layer on the balloon catheter comprising a composite of polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer. The invention further provides an implantable medical device wherein the polymer is biodegradable. The invention further provides an implantable medical device wherein the polymer is a bioabsorbable polymer. The invention further provides an implantable medical device wherein the polymer is selected from the group consisting of polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly(etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof. The invention further provides an implantable medical device wherein the concentration of the first active agent based on the surface area of the balloon catheter ranges from about 1 to about 5 μg/mm$^2$, and the concentration of the optional second active agent based on the surface area of the balloon ranges from about 1 to about 5 μg/mm$^2$. The invention further provides an implantable medical device wherein the ratio which is in the range selected from the group consisting of about 1:5, about 1:2, and about 1:1 resveratrol to quercetin by weight percent. The invention further provides an implantable medical device wherein the first and second active agents are in a ratio which is selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides an implantable medical device wherein the ratio of the first and second active agents to polymer is in a range selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides an implantable medical device wherein the composite includes a plurality of layers. The invention further provides an implantable medical device wherein the ratio of pharmaceutically active substance to polymer is varied in some of the layers. The invention further provides an implantable medical device wherein each of the active agents may have different release profiles. The invention further provides an implantable medical device wherein the release profile of the active agents may be selected between rapid and delayed. The invention further provides an implantable medical device wherein a rapid profile coating releases an active agent substantially within one to a few hours. The invention further provides an implantable medical device wherein a delayed profile coating releases an active agent and/or agents over a period of at least one month, at least two months, at least six months, or at least one year.

The invention provides the use of a catheter having an expandable balloon catheter coated with a selected polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer in the manufacture of a medicament for the treatment or prevention atherosclerosis, stenosis, restenosis, smooth muscle cell proliferation, platelet cell activation and other clotting mechanisms, occlusive disease, or other abnormal lumenal cellular proliferation condition in a location within the body of a patient.

The invention provides a catheter having an expandable balloon catheter coated with a selected polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer for use in treatment or prevention atherosclerosis, stenosis, restenosis, smooth muscle cell proliferation, platelet cell activation and other clotting mechanisms, occlusive disease, or other abnormal lumenal cellular proliferation condition in a location within the body of a patient.

The invention provides a method of for treating or preventing atherosclerosis, stenosis, restenosis, smooth muscle cell proliferation, platelet cell activation, or other abnormal lumenal cellular proliferation condition in a location within the body of a patient in a luminal passage in a subject comprising: selecting a catheter having an expandable balloon catheter; coating the balloon catheter with a selected polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer; routing the catheter through a predetermined length of the luminal passage; and expanding the balloon at one or more selected positions along the predetermined length. The invention further provides a method wherein the polymer is selected from the group consisting of polystyrene-polyisobutylene block copolymers, polyethylene terephthalate, poly (lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly (n-butyl methacrylate), poly(ethylene-co-vinyl acetate), poly (vinylidene fluoride-co-hexafluoropropene), poly (etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof. The invention further provides a method wherein the concentration of the first active agent based on the surface area of the balloon catheter ranges from about 1 to about 5 µg/mm2, and the concentration of the optional second active agent based on the surface area of the balloon ranges from about 1 to about 5 µg/mm2. The invention further provides a method wherein the ratio of first and second active agents is in a range selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a method wherein the ratio of the first and second active agents to polymer is in a range of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent. The invention further provides a method wherein the ratio first and second active agents is in the range selected from the group consisting of about 1:5, about 1:2, and about 1:1 resveratrol to quercetin by weight percent. The invention further provides a method wherein the composite includes a plurality of layers. The invention further provides a method wherein the ratio of pharmaceutically active substances to polymer is varied in some of the layers. The invention further provides a method wherein each of the active agents may have different release profiles. The invention further provides a method wherein the release profile of the active agents may be selected between rapid and delayed. The invention further provides a method wherein a rapid profile coating releases an active agent substantially within one to a few hours. The invention further provides a method wherein a delayed profile coating releases an active agent and/or agents over a period of at least one month, at least two months, at least six months, or at least one year.

The invention provides a method of electrospraying nanoparticles on to a surface of an implantable medical device selected from the group consisting of a catheter having an expandable balloon and an intravascular stent, the method comprising: providing a combination in solvent of a polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof, dispersed within the polymer combination in solvent to an inner capillary of a coaxial capillary spray nozzle; providing a solvent to an outer capillary of the coaxial capillary spray nozzle; providing a difference in electrical potential between an exit tip of a coaxial capillary spray nozzle and the surface to cause electrospray from the nozzles such that nanoparticles are formed and adhered to the surface to provide a desired drug release profile. The invention further provides a method wherein the polymer is selected from the group consisting of polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly(etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof.

The invention further provides a method wherein each of the two active agents may have different release profiles. The invention further provides a method wherein the release profile of the active agent may be selected between rapid and delayed. The invention further provides a method wherein a rapid profile coating releases an active agent substantially within one to a few hours. The invention further provides a method wherein a delayed profile coating releases an active agent and/or agents over a period of at least one month, at least two months, at least six months, or at least one year.

Invention provides a method of coating an implantable medical device selected from the group consisting of a catheter having an expandable balloon and an intravascular stent, the method comprising: providing a coating solution comprising a polymer and a first active agent selected from the group consisting of resveratrol, pharmaceutically acceptable salts, and pharmaceutically acceptable derivatives thereof, and an optional second active agent selected from the group consisting of quercetin, pharmaceutically acceptable salts, and pharmaceutically acceptable derivatives thereof; providing an implantable medical device; submerging the entire implantable medical device, or an entire section of the implantable medical device, in the coating solution; withdrawing the implantable medical device from the coating solution; and drying the implantable medical device. The invention further provides a method wherein the polymer is selected from the group consisting of polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly(etherurethane urea), silicones, acrylics, epoxides, polyesters, polyurethanes, desaminotyrosine polyarylate, Parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof. The invention further provides a method wherein each of the active agents may have different release profiles. The invention further provides a method wherein the release profile of the active agents may be selected between rapid and delayed. The invention further provides a method wherein a rapid profile coating releases an active agent substantially within one to a few hours. The invention further provides a method wherein a delayed profile coating releases an active agent and/or agents over a period of at least one month, at least two months, at least six months, or at least one year.

BRIEF DESCRIPTION OF SEVERAL VIEWS OF THE DRAWINGS

FIGS. 14A, 14C, 14E) and 20,000× magnification (right; FIGS. 14B, 14D, 14F). Images FIG. 14A and FIG. 14B are quercetin containing arbIBS nanoparticles coated using a closed morphology, while images FIG. 14C and FIG. 14D are coated using an open morphology. FIG. 14E and FIG. 14F are resveratrol containing arbIBS nanoparticles coated using a closed morphology. All polymer applications were by ElectroNanospray™ process.

DETAILED DESCRIPTION OF THE INVENTION

Figure 1:
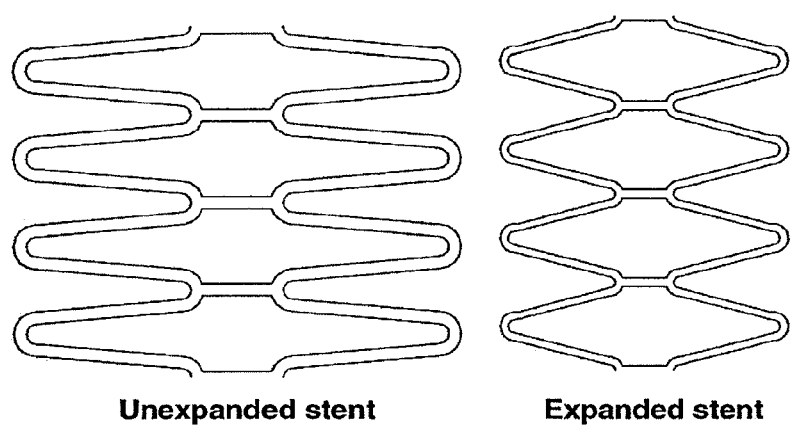
FIG. 1 is a diagram of a stent design according to an embodiment of the present invention.
Figure 2:
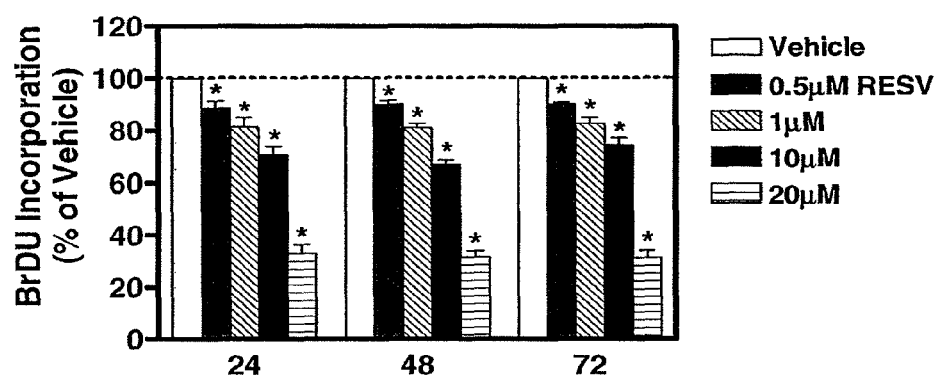
FIG. 2 is a bar chart showing the effects of resveratrol on proliferation of rat aortic vascular smooth muscle cells according to the present invention.
Figure 3:
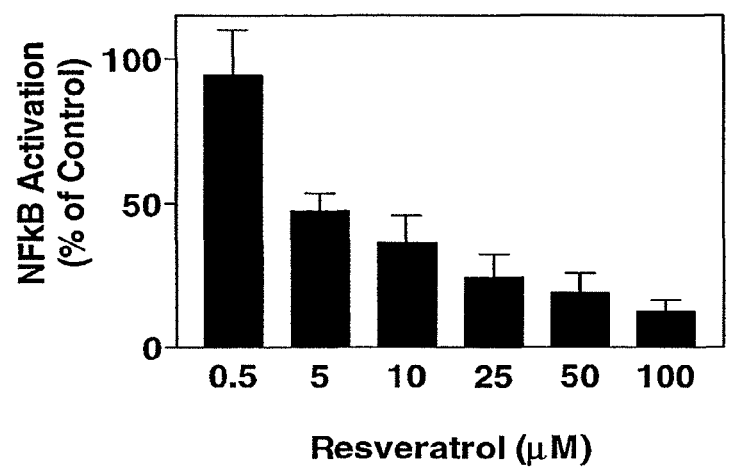
FIG. 3 is a bar chart showing the effect of resveratrol on NFκB activation in vascular smooth muscle cells
Figure 4:
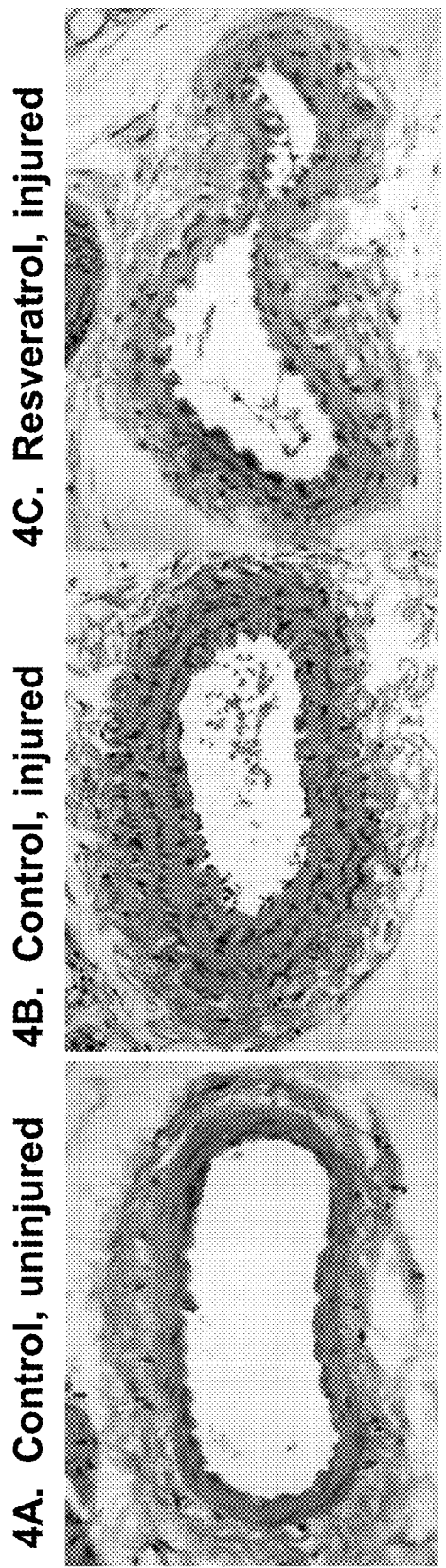
FIG. 4 is a set of three digital photographs showing carotid arteries from wildtype controls, wildtype mice subjected to endothelial denudation, and wildtype mice administered resveratrol for 4 weeks and subjected to endothelial denudation according to the present invention.
Figure 5:
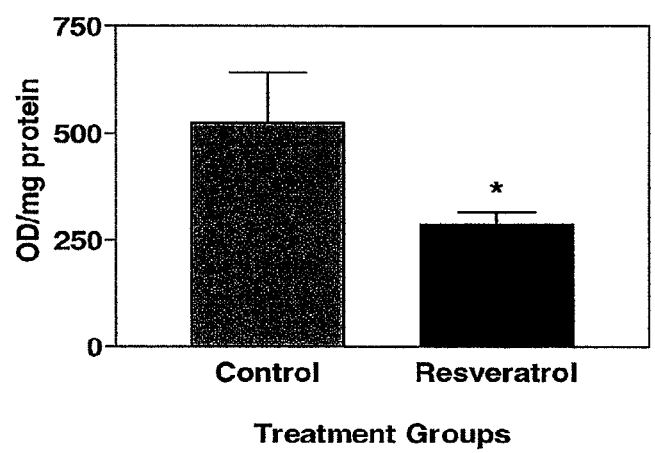
FIG. 5 is a bar chart showing the effects of oral resveratrol administration on NFκB activation in mouse aorta after carotid artery endothelial denudation according to the present invention.
Figure 6:
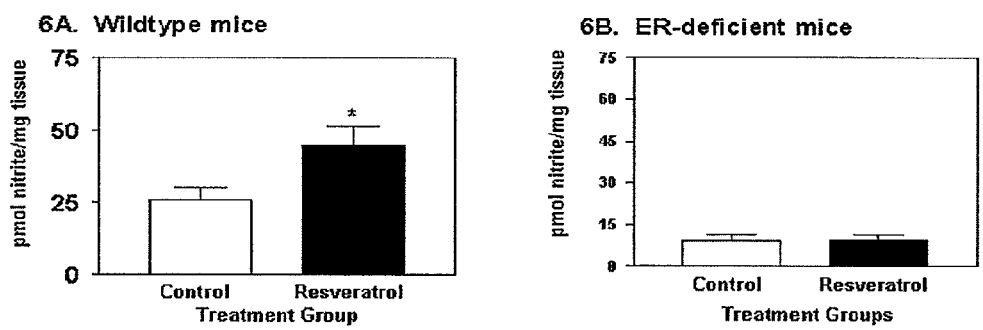
FIG. 6 is a set of bar charts showing the effects of oral resveratrol administration on vascular nitric oxide production, as assessed by measurement of its stable metabolite, nitrite, in aortas of either wildtype mice or ER-deficient mice according to the present invention.
Figure 7:
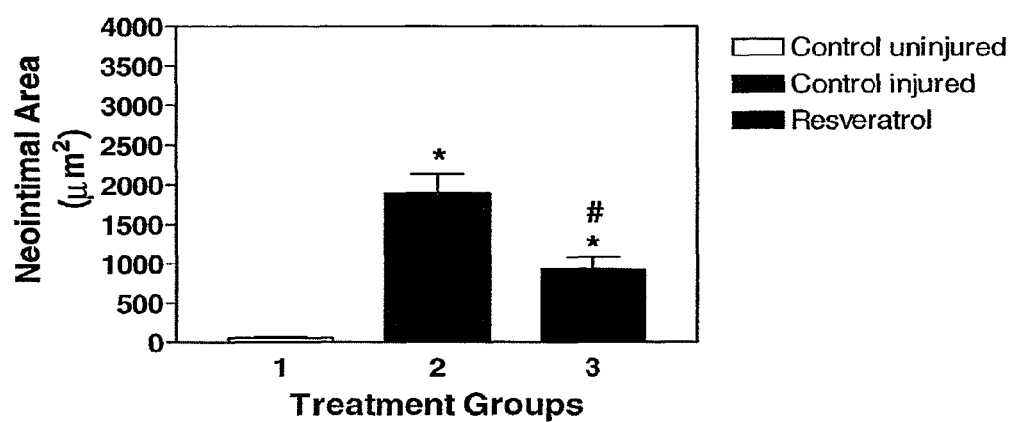
FIG. 7 is a bar chart showing the effect of resveratrol on neointimal area in mice.
Figure 8:
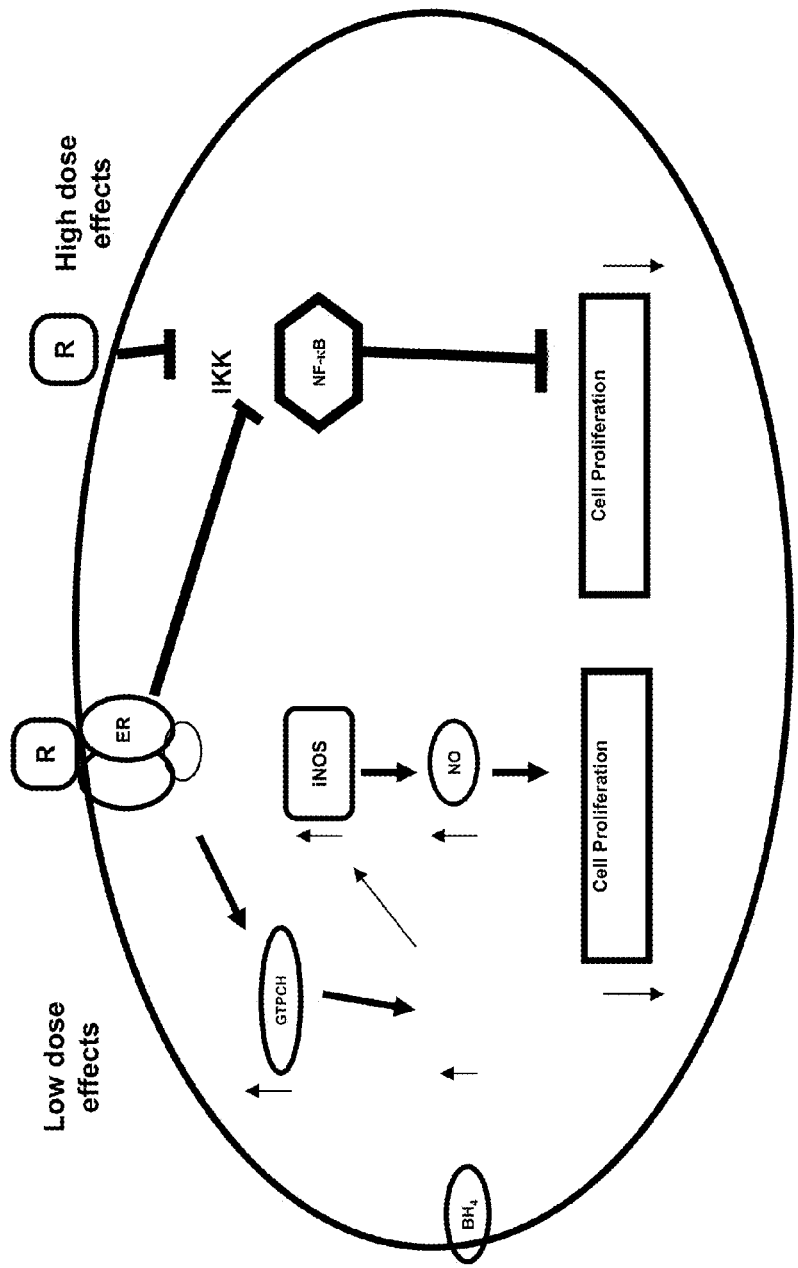
FIG. 8 is a schematic showing the mechanism for resveratrol-mediated inhibition of VSMC proliferation according to the present invention.
Figure 9:
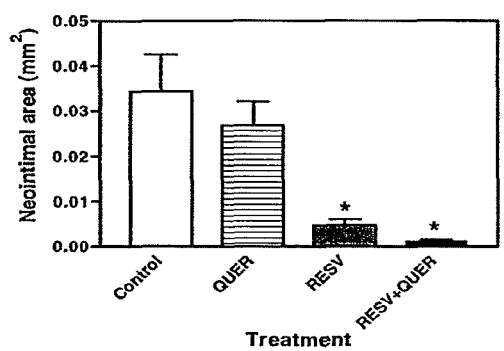
FIG. 9 is a bar chart showing the effects of oral administration with 50 mg/kg resveratrol (RESV), 10 mg/kg quercetin (QUER), or resveratrol plus quercetin on neointimal areas in mice subjected to the carotid artery injury procedure. Values represent means+SEM. ANOVA revealed a significant effect of treatment. *Denotes significance compared to controls. Neointimal area was determined by subtracting the luminal area from the area encircled by the internal elastic lamina.

Coated Stent Reducing SMC Proliferation and Platelet Activity

The following description should be viewed in the eyes of someone who is familiar with the state-of-the-art in this field; specific technology should not be considered limiting but should be taken as use of state-of-the-art at a moment in time. The present invention is capable of embodiments in many different forms. Preferred embodiments of the invention are disclosed with the understanding that the present disclosure is to be considered as exemplifications of the principles of the invention and are not intended to limit the broad aspects of the invention to the embodiments illustrated. In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

The present invention relates generally to the maintenance of blow flood through stenotic areas using drug eluting stents and/or other medical devices; and, to increased length of time of blood flow without restenosis in these areas.

Also, the present invention relates to drug-releasing stents for maintenance of blow flood through stenotic areas and to increased length of time of blood flow without restenosis. Preferably the stents and/or other medical devices of the present invention is/are coated with agents that can include but are not limited to phytochemicals such as polyphenols. One exemplary embodiment is a DES coated with a single agent, especially where that agent is resveratrol, which results in maintenance of blood flow and decreased restenosis. Additional embodiments would have multiple agents, preferably resveratrol and quercetin, coating the stent to maintain blood flow and decrease restenosis.

According to one embodiment of the present invention, the resveratrol/quercetin combination will have equal or better efficacy with fewer side effects compared to rapamycin- or paclitaxel-coated stents. The resveratrol/quercetin combination will likely block more pathways involved in restenosis. For example, the combination should inhibit VSMC proliferation, platelet activation, and inflammatory responses, and may even promote endothelial function. None of the currently-used DES promotes endothelial function or re-endothelialization.

Resveratrol

The invention, as noted above, involves the administration of resveratrol to an individual in order to prevent restenosis and/or the progression or recurrence of coronary heart disease.

Resveratrol may be administered in natural form, i.e., as isolated from grape skins, wine or other plant-derived compositions, or it may be administered as chemically synthesized in the laboratory (e.g., using the methods of Moreno-Manas et al., Jeandet et al., or Goldberg et al. (1994), cited earlier herein), or as obtained commercially, e.g., from the Sigma Chemical Company (St. Louis, Mo.).

The resveratrol active agent may be administered in the form of a pharmacologically acceptable salt, ester, amide, prodrug or analog, or as a combination thereof. However, conversion of an inactive ester, amide, prodrug or analog to an active form must occur prior to or upon reaching the target tissue or cell. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature (see U.S. Pat. No. 6,022,901).

Formula I

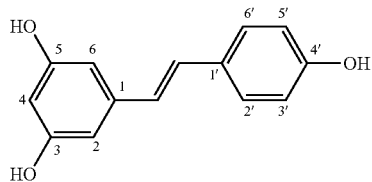

Non-limiting examples of derivatives of cis- and trans-resveratrol are those in which the hydrogen of one or more of the compounds' hydroxyl groups is replaced to form esters or ethers (for example, see Formula I). Ether formation examples include, but are not limited to, the addition of alkyl chains such as methyl and ethyl groups, as well as conjugated mono- or disaccharides such as glucose, galactose, maltose, lactose and sucrose. Additional modifications at the hydroxyl groups might include glucuronidation or sulfation.

Esterification products include, but are not limited to, compounds formed through the addition of amino acid segments such as RGD or KGD or other compounds resulting from the reaction of the resveratrol hydroxyl groups with other carboxylic acids.

Additional derivatives include, but are not limited to, those compounds that result from the oxidative dimerization of or functional group addition to the parent resveratrol compound or to a functionalized resveratrol variant. Examples of these compounds include materials resulting from the addition of hydroxyl, methoxy and ethoxy groups at the 4, 2', and 3' positions. Dimerization results from the reaction of the ethane bond of one resveratrol molecule with one of the hydroxyl groups on a second resveratrol molecule resulting in the formation of a fused ring system. Alkylation at the 4, 2', and 3' positions creates other derivatives through the addition of groups including, but not limited to, methyl, ethyl, and propyl, as well as the addition of larger carbon chains such as 4-methyl-2-pentene, 4-methyl-3-pentene and isopentadiene.

Additional derivatives include, but are not limited to, compounds that arise from the loss of any of the hydroxyl groups of the parent molecule, addition of hydroxyl groups at alternate positions, and any compound that may arise from the previously mentioned reactions to provide a functionalized variant of the dehydroxylated compound.

Examples of Resveratrol Derivatives

Formula II

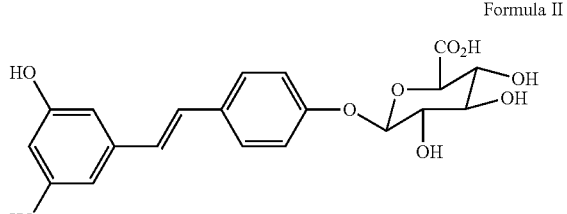

Formula III

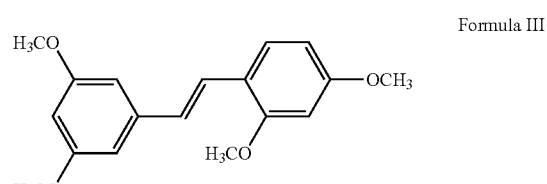

Formula IV

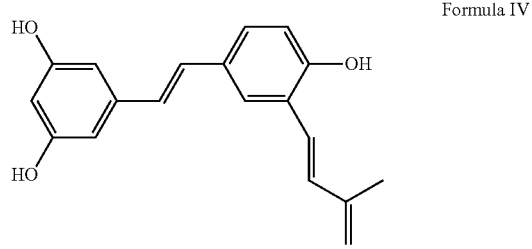

Formula V

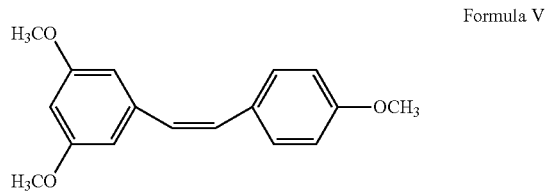

Formula VI

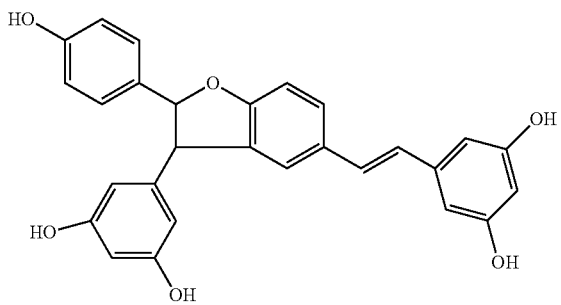

Additional Uses for Resveratrol

Resveratrol may be involved in many pathways of restenosis. Thus, according to the present invention, resveratrol may address many if not all targets causing a problem from restenosis. For instance, it provides anti-inflammatory benefits and promotes endothelial cell function. Reports have shown that resveratrol stimulates the growth of endothelial progenitor cells, both in vivo and in vitro (see J. Gu, et al., 2006, Effects of resveratrol on endothelial progenitor cells and their contributions to reendothelialization in intima-injured rats. J Cardiovasc Pharmacol., 47(5): 711-721). This may be a key step in re-endothelialization.

Resveratrol also increases endothelial nitric oxide synthase activity (see Wallerath T et al., "Resveratrol, a polyphenolic phytoalexin present in red wine, enhances expression and activity of endothelial nitric oxide synthase." Circulation. 2002 Sep. 24; 106(13):1652-8.) Further, resveratrol enhances endothelium-dependent vasorelaxation (Rush J W, Quadrilatero J, Levy A S, Ford R J. Chronic resveratrol enhances endothelium-dependent relaxation but does not alter eNOS levels in aorta of spontaneously hypertensive rats. Exp Biol Med (Maywood). 2007 June; 232(6):814-22). Therefore, utilizing resveratrol in a DES and/or other medical device according to the present invention provides a multi-faceted approach to reducing restenosis and improving blood flow after stent implantation.

Quercetin

Another exemplary compound for use in the compositions of the present invention is quercetin or an analog of quercetin. Quercetin is typically found in plants as glycone or carbohydrate conjugates. Quercetin itself is an aglycone or aglucon. That is, quercetin does not possess a carbohydrate moiety in its structure. Analogs of quercetin include its glycone conjugates include rutin and thujin. Rutin is also known as quercetin-3-rutinoside. Thujin is also known as quercitrin, quercetin-3-L-rhamnoside, and 3-rhamnosylquercetin. Onions contain conjugates of quercetin and the carbohydrate isorhamnetin, including quercetin-3,4'-di-O-beta glucoside, isorhamnetin-4'-O-beta-glucoside and quercetin-4'-O-beta-glucoside. Quercetin itself is practically insoluble in water. The quercetin carbohydrate conjugates have much greater water solubility then quercetin.

Quercetin is known chemically as 2-(3,4-dihydroxyphenyl)-3,5,7-trihydroxy-4H-1-benzopyran-4-one and 3,3',4',5,7-pentahydroxy flavone.

Quercetin is a phenolic antioxidant and has been shown to inhibit lipid peroxidation. In vitro and animal studies have shown that quercetin inhibits degranulation of mast cells, basophils and neutrophils. Such activities account, in part, for quercetin's anti-inflammatory and immunomodulating activities. Other in vitro and animal studies show that quercetin inhibits tyrosine kinase and reduces the activation of the inflammatory mediator, NF-κB. Further activities of quercetin include anti-viral and anti-cancer activity. Quercetin is further known to inhibit aldose reductase. A quercetin or an analog thereof for use in the present invention can be an inhibitor of tyrosine kinases. The most important biologic activities of quercetin are its inhibition of platelet activation plus its anti-inflammatory properties, as the interaction of these two effects can reduce the incidence of thrombogenesis associated with current generation DES. Quercetin inhibits both platelet activation and platelet aggregation. It enhances platelet-derived nitric oxide to inhibit the activation of a protein kinase C-dependent NADPH oxidase. In addition, quercetin inhibits platelet aggregation through its inhibition of phosphoinositide kinase. Further properties of quercetin or its analogs that are relevant in the context of the present invention include: inhibition of cell cycle, inhibition of smooth muscle cell proliferation and/or migration. Suitable analogs/derivatives of quercetin include its glycone conjugates rutin and thujin (See U.S. Patent Application Publication No. 2007/0212386 (Patravale et al.)).

Quercetin and/or its analogs may be capable of exerting the above activities when used singly. However, the above properties of quercetin and/or its analogs may be further enhanced by exploiting the synergy between quercetin and/or its analogs and further therapeutic agents (as disclosed herein), such as resveratrol and/or its derivatives.

In one embodiment, the combination of polymer and pharmaceutically active agent comprise a combination of pharmaceutically active agents. If more than one pharmaceutically active agent is used, they can be present in combination in the same layer, or in separate polymer layers. Exemplary combinations include resveratrol plus quercetin separately or in combination in one or more coatings and resveratrol or quercetin alone or in combination in one or more coatings.

Formula VII

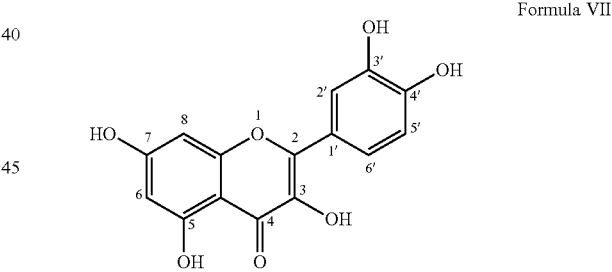

Exemplary derivatives of quercetin are those in which the hydrogen of one or more of the compounds' hydroxyl groups, most commonly the 3 hydroxyl is replaced to form esters or ethers (see for example Formula VII). Ether formation examples include, but are not limited to, the addition of alkyl chains such as methyl and ethyl groups, as well as deoxy sugars such as fucose and rhamnose. Esterification products include, but are not limited to; compounds formed through the reaction of carboxylic acid containing materials such as acetic acid, propionic acid and palmitic acid. Urethane derivatives of quercetin include, but are not limited to; amino acid ester carbamates formed by the addition of materials such as benzyl 2-isocyanatoacetate and (S)-methyl 2-isocyanatopropanoate.

Additional quercetin derivatives include, but are not limited to, compounds that can be described as metabolites formed by the addition of sugar-like derivatives such as glucuronyl groups at any of the hydroxyl positions. Examples of these metabolites include 7-O-glucuronyl-quercetin and 3'-O-glucuronyl-quercetin.

Additional derivatives include, but are not limited to, compounds that arise from the loss of any of the hydroxyl groups of the parent molecule, addition of hydroxyl groups at alternate positions, and any compound that may arise from the previously mentioned reactions to provide a functionalized variant of the dehydroxylated compound.

Examples of Quercetin Derivatives

Formula VIII

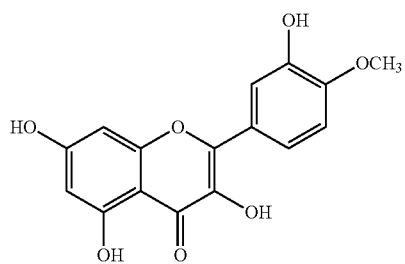

Formula IX

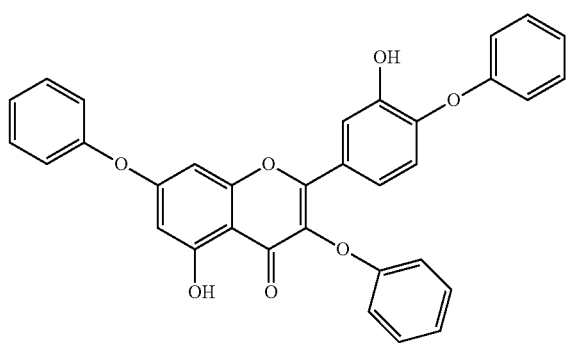

Formula X

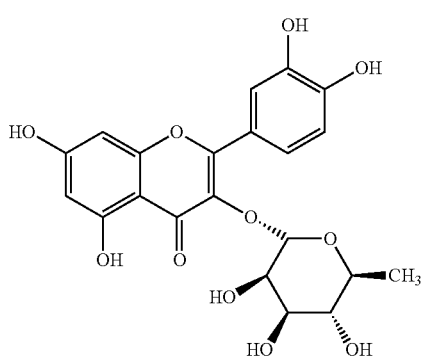

Formula XI

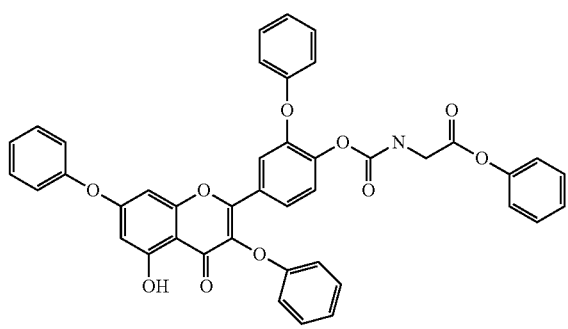

Resveratrol and Quercetin

In an exemplary embodiment, resveratrol plus a small concentration of quercetin are incorporated onto a DES and/or other medical device to maintain blow flood through stenotic areas using stents; and, to increased length of time of blood flow without restenosis in these areas.

For more information on the use of resveratrol in the treatment of restenosis through methods other than drug-eluting stents, see U.S. Pat. No. 6,022,901, to David William Goodman, titled "Administration of resveratrol to prevent or treat restenosis following coronary intervention", which is herein incorporated by reference in its entirety.

Resveratrol is a polyphenol that has been linked to the reported cardioprotection of red wine consumption. The reported cardioprotective effects of red wine consumption was prompted by epidemiological studies documenting the "French Paradox," a term coined to describe the reduced incidence of death due to CHD in areas of southwest France. Inhabitants of this area exhibit increased serum cholesterol and blood pressure and eat more lard and butter than do Americans, yet suffer 40% fewer deaths due to CHD than other western societies. This paradoxical effect is attributed to their daily consumption of red wine. While epidemiological studies suggest a decreased risk of CHD in populations regularly consuming alcohol, considerable data indicate that wine provides greater protection as compared to other alcoholic beverages.

Resveratrol is a phytoalexin polyphenol found in foods such as grapes, mulberries, peanuts, and grapevine. Within the grape itself, resveratrol is most abundant in the skin (ca. 50-100 μg/gm. One fluid ounce of red wine provides ~160 μg resveratrol. The rapid conjugation of resveratrol to form glucuronides and sulfates has been argued as evidence that orally administered resveratrol concentrations cannot approach therapeutically useful levels. However, immediately after consumption, resveratrol can be measured in the plasma, heart, liver, and kidney. Chronic consumption further increases levels of resveratrol in tissues such as the heart and liver.

Quercetin is also a polyphenol present in red wine and it is likewise reported to exert protection against atherosclerosis. From a pharmacological point of view, an exemplary drug combination of the present invention, resveratrol and quercetin, appears reasonable, red wine is actually a combination of low levels of many bioactive polyphenols that act synergistically to exert the effects observed clinically for chronic red wine consumption.

Prior reports by other laboratories have indicated that resveratrol acts through a variety of mechanisms to promote vascular health. As an antioxidant polyphenol, it limits the oxidation of low-density lipoprotein, thus inhibiting fatty streak formation. It furthermore exhibits anti-inflammatory effects through an inhibition of NFκB activation. Several labs have demonstrated that resveratrol promotes endothelial function by increasing eNOS activity, and a recent report suggests that the mechanism for this effect is an increase in eNOS phosphorylation. Resveratrol also promotes endothelial protection against oxidant injury, likely via an inhibition of the activation of NADPH oxidase. Finally, resveratrol inhibits adhesion of inflammatory cells to the vascular endothelium by inhibiting the expression of adhesion molecules.

Prior reports demonstrate resveratrol's efficacy in inhibiting proliferation of vascular smooth muscle cells (VSMC). For example, in VSMC stimulated with the mitogens endothelin-1 and platelet-derived growth factor, resveratrol inhibited cell cycle traverse, and in coronary artery smooth muscle, resveratrol inhibited endothelin-1-induced map kinase stimulation.

The mechanisms for these effects are due in part to a resveratrol-mediated ER activation that culminates in an upregulation of tetrahydrobiopterin ($BH_4$) biosynthesis. The inventors have demonstrated that the resulting increase in levels of $BH_4$, a known NOS cofactor, promoted an elevation in NO concentration that culminated in cell cycle arrest. Effects on NO concentration are dependent upon an increase in inducible nitric oxide synthase (iNOS) activity, but not its expression. In addition to this novel ER-dependent pathway, the current invention also shows that resveratrol inhibits NFκB activation very potently.

Thus, according to the present invention, resveratrol exerts pleiotropic effects on VSMC proliferation, enhancing NO production through an ER-dependent pathway, but also inhibits NFκB activation through an ER-independent pathway. It is the cooperativity between these two pathways that accounts for the observed effects on VSMC proliferation.

Quercetin is an inhibitor of both platelet and NFκB activation. The addition of quercetin to the DES of the present invention should potentiate the effects of resveratrol on VSMC proliferation by boosting the inhibitory effects on NFκB activation. Further, strong inhibition NFκB should also potentiate resveratrol-mediated inhibition of the inflammatory component of restenosis. Addition of quercetin should also limit platelet activation, which is a part of the inflammatory response to balloon angioplasty and stent implantation that leads to restenosis. Alternatively, another agent or agents which inhibit platelet activation and/or aggregation could be utilized in place of quercetin with resveratrol. Such alternative options include, but are not limited to, aspirin, ticlopidine, clopidogrel, dipyridamole, and the like.

Resveratrol has same binding site as estradiol and behaves as an ER-alpha agonist, however, it has a lower binding affinity than estradiol. This provides protection against estrogenic side effects, such as alternation of the female menstrual cycle and feminization side-effects in males.

Alternative Drug Delivery Mechanisms

Oral dosing of resveratrol is described in U.S. Pat. Nos. 6,022,901 and 6,211,247 to David William Goodman titled "Administration of resveratrol to prevent or treat restenosis following coronary intervention", which are herein incorporated by reference in their entirety. However, positive effects from oral dosing studies in animal models would require humans to ingest ~3 g/day in a 60 kg human. Therefore, a drug releasing stent and/or other medical device should work better than oral dosage because of its localized targets. Regardless, the present invention contemplates oral delivery of a therapeutic amount of both resveratrol and quercetin to prevent or treat restenosis.

Devices

In one embodiment, the device treats narrowing or obstruction of a body passageway in a subject in need thereof. In another embodiment, the method comprises inserting the device into the passageway, the device comprising a generally tubular structure, the surface of the structure being coated with a composition disclosed herein, such that the passageway is expanded. In the method, the body passageway may be selected from arteries, veins, lacrimal ducts, trachea, bronchi, bronchiole, nasal passages, sinuses, eustachian tubes, the external auditory canal, oral cavities, the esophagus, the stomach, the duodenum, the small intestine, the large intestine, biliary tracts, the ureter, the bladder, the urethra, the fallopian tubes, uterus, vagina, the vasdeferens, and the ventricular system.

Exemplary devices include, but are not limited to, stents, balloon components of balloon catheters, catheters, guidewires, sutures, staples, anastomosis devices, vertebral disks, bone pins, suture anchors, hemostatic barriers, clamps, screws, plates, clips, vascular implants, urological implants, tissue adhesives and sealants, tissue scaffolds, bone substitutes, intraluminal devices, and vascular supports. For example, the device can be a cardiovascular device, such as venous catheters, venous ports, tunneled venous catheters, chronic infusion lines or ports, including hepatic artery infusion catheters, pacemakers and pace maker leads, and implantable defibrillators. Alternatively, the device can be a neurologic/neurosurgical device such as ventricular peritoneal shunts, ventricular atrial shunts, nerve stimulator devices, dural patches and implants to prevent epidural fibrosis post-laminectomy, and devices for continuous subarachnoid infusions. The device can be a gastrointestinal device, such as chronic indwelling catheters, feeding tubes, portosystemic shunts, shunts for ascites, peritoneal implants for drug delivery, peritoneal dialysis catheters, and suspensions or solid implants to prevent surgical adhesions. In another example, the device can be a genitourinary device, such as uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy, central venous catheters.

Other exemplary devices include, but are not limited to, prosthetic heart valves, vascular grafts ophthalmologic implants (e.g., multino implants and other implants for neovascular glaucoma, drug eluting contact lenses for ptergiums, splints for failed dacrocystalrhinostomy, drug eluting contact lenses for corneal neovascularity, implants for diabetic retinopathy, drug eluting contact lenses for corneal injury or high risk corneal transplants), otolaryngology devices (e.g., ossicular implants, Eustachian tube splints or stents for glue ear or chronic otitis as an alternative to transtempanic drains), plastic surgery implants (e.g., breast implants or chin implants), and catheter cuffs and orthopedic implants (e.g., cemented orthopedic prostheses).

Another exemplary device according to the invention is a stent, such as a stent comprising a generally tubular structure. A stent is commonly used as a tubular structure disposed inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

An exemplary stent is a stent for treating narrowing or obstruction of a body passageway in a human or animal in need thereof. "Body passageway" as used herein refers to any of number of passageways, tubes, pipes, tracts, canals, sinuses or conduits which have an inner lumen and allow the flow of materials within the body. Representative examples of body passageways include arteries and veins, lacrimal ducts, the trachea, bronchi, bronchiole, nasal passages (including the sinuses) and other airways, eustachian tubes, the external auditory canal, oral cavities, the esophagus, the stomach, the duodenum, the small intestine, the large intestine, biliary tracts, the ureter, the bladder, the urethra, the fallopian tubes, uterus, vagina and other passageways of the female reproductive tract, the vasdeferens and other passageways of the male reproductive tract, and the ventricular system (cerebrospinal fluid) of the brain and the spinal cord. Exemplary devices of the invention are for these above-mentioned body passageways, such as stents, e.g., vascular stents. There is a multiplicity of different vascular stents known in the art that may be utilized following percutaneous transluminal coronary angioplasty.

Any number of stents may be utilized in accordance with the present invention and the invention is not limited to the specific stents that are described in exemplary embodiments of the present invention. The skilled artisan will recognize that any number of stents may be utilized in connection with the present invention. In addition, as stated above, other medical devices may be utilized, such as e.g., orthopedic implants.

Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor, and U.S. Patent Application Publication No. 20050186248 (Hossainy).

According to one embodiment of the present invention, the stent has expandable radial struts (FIG. 1). The number of struts and cells may vary with the size of the stent, also. For a detailed description of such a stent, please see U.S. Pat. No. 5,843,172 to John Y. Yan, titled "Porous medicated stent", which is herein incorporated by reference in its entirety. For other examples such a stent, please see U.S. Pat. No. 6,083,257 to Alistair Stewart Taylor, Peter William Stratford, Yiannakis Petrou Yianni, and Matthew John Woodroffe titled "Braided Stent", which is herein incorporated by reference in its entirety; and, U.S. Pat. No. 6,471,979, to Gishel New, Jeffrey W. Moses, Nicholas Kipshidze, Gary S. Roubin, and Martin B. Leon, titled "Apparatus and method for delivering compounds to a living organism", which is herein incorporated by reference in its entirety. The stents and/or other medical devices may be prepared by an initial dip coating with a silane ester primer, followed by sequential layering of a biocompatible polymer preparation containing 5-20% resveratrol, which will likewise be accomplished by a dip-coating technique; the biocompatible polymer preparation can be a hydrophilic polyurethane. An additional layer of polymer can be placed over the final layer of drug coating for a more controlled drug delivery. All of the described techniques for stent construction, with the exception of the resveratrol/quercetin formulation, are well-known to the art.

Drug Eluting Balloon Catheters and Other Devices

The invention also provides a drug coated balloon in for example, a catheter, particularly where the drug has anti-inflammatory, anti proliferative or anti-thrombotic capability or can prevent collagen induced platelet aggregation.

The catheter balloon is typically coated with layers one or more of the polymers disclosed elsewhere in this specification particularly where the drug is sequestered within one or more of the polymer coating materials. Preferred polymer coating materials include Poly L-Lactide polymer (PLLA), poly(lactide-co-glycolide) (PLGA), poly(l-lactide-co-trimethylene carbonate), poly(d,l-lactide-co-trimethylene carbonate), polyvinyl alcohol (PVA) and polyalkylene glycols (PAG) such as polyethylene glycol (PEG), albumin, gelatin, starch, cellulose, dextrans, polysaccharides, fibrinogen, poly(D,L lactide), poly(D,L-lactide-co-glycolide), poly(glycolide), poly(hydroxybutyrate), poly(alkylcarbonate), poly(orthoesters) and any of the polymers disclosed herein for use in covalent binding of drugs having a nucleophilic group (e.g. hydroxyl or amino) available for reaction with a complementary electrophilic group of the polymer material. The selected polymer coatings can be mixed, combined or covalently bound to the selected bioactive drug in any desired concentration of selected drug. Two or more polymers can be combined with each other to form a polymer matrix. The balloon can contain multiple coatings or layers of such polymers, at least one of the layers or coatings containing a selected drug.

Other polymer materials may be used alone or together with any of the foregoing polymers as disclosed for example in Patent Cooperation Treaty application PCT/IN02/00173 03018082, the disclosure of which is incorporated herein by reference as if fully set forth herein.

The drug or drugs that is/are selected for inclusion in the coating on the stents and/or other medical devices may or may not be covalently bound to the coating polymer. Examples of the drug or drugs which may be included in the coating, include but are not limited to, resveratrol and quercetin for use in/on a coating on a balloon catheter. Any other of the drugs described in this specification can alternatively be used depending on the treatment desired.

Dip coating techniques may be used for coating the surface of a balloon although other methods may also be employed such as spray coating. Coating is typically comprised of a single layer but may also comprise multiple layers depending on the content and release profile of drug contained in the coating. The surface may also be coated with micro or nano-formulations of the active agents. These may be pure active agent nanoparticles adhered to the surface or released from beneath a polymeric film or active agents encapsulated in polymeric micro- or nanospheres or other carriers such as liposomes. Polymeric capsules may either be rupturable to release their contents, may release the active agents after enzymatic or hydrolytic break down or release the active agents by diffusion release formulations.

Coated balloons are useful in revascularization, catheterization, balloon expansion and stent delivery procedures and methods described herein. In a stent delivery procedure for example, a drug coated balloon according to the invention may also incidentally deliver drugs to vessel areas that are not situated at the localized situs of implant of a stent. Such incidental delivery of drug from the surface of the balloon is of particular utility for small and tortuous vessel passages leading up to the site of interest. Furthermore, healing and re-endothelialization of stent struts that do not carry antiproliferative agents can be facilitated by the use of drug coated balloons.

On pressurized contact of the surface of the balloon with a blood vessel wall either as a result of stent delivery or otherwise, the drug containing polymer coating will adhere to the blood vessel wall surface and release the drug either over a very short period of time, e.g. less than about 45 seconds, or over a longer period of time as described below, e.g. over less than about 8 minutes, depending on the selection of the coating material(s), whether the drug is covalently bound, the miscibility/affinity of the drug for the coating material and the concentration of the selected drug in the coating.

As a specific example, the surface of a stent, catheter balloon, or other medical device is coated with 0.1 to 15 µg of resveratrol and/or quercetin per square millimeter of device surface to enable immediate release of the drug on inflation. The coating resulted in a very slight increase in profile but no recognizable change in flexibility. The release profile for compound or compounds in the coating on the surface of a stent, catheter balloon, and/or other medical device, is in a time period of between about 20 and about 40 seconds, about 1 min to 100 minutes, about 1 hour to 20 hours, about 1 day to 1 month, about 1 day to 10 days, about 1 day to about 30 days, about 1 day to about 2 months, about 1 day to about 6 months, about 1 day to about 6 months, about 1 day to about 1 year. Non limiting examples of delayed profile coating release an active agent and/or agents over a period of at least one month, at least two months, at least six months, or at least one year, after implantation.

Polymers

The invention is directed to thin coatings for medical devices, more specifically an implantable medical device, for example a stent and/or other medical device. In accordance to one embodiment, the invention is specifically directed to a coating for a stent. The stent can be a self-expandable stent or a radially expandable stent. In others embodiments, the stent can have a coil configuration or be made from a wire or fiber-type body. The stent body can be made from a metallic material, polymeric material, or a combination of metallic or polymeric material. The combination can be in a layered, disbursed, blended or conjugated form. In some embodiments, the metal or polymer can be biodegradable such that the stent is intended to remain at the implantation site for a temporary duration of time. Biodegradable, bioerodable, bioabsorbable, etc. are terms which are used interchangeably unless otherwise specifically intended. The stent may have, for example, a polymer body made from one or a combination of polymers. In some embodiments, the stent is from about 5 mm in length to about 40 mm in length. In some embodiments, the stent is at least 40 mm in length. See U.S. Patent Application Publication No. 2007/0299511 (Gale).

A thin coating may be disposed on the surface of the structural element or strut. The coating can be deposited on the outer surface, inner surface and the side walls of the strut. In some embodiments, the coating is exclusively on the outer surface, and not the inner surface or the side walls. In some embodiments, the coating can be on the outer surface and at least a portion of the sidewalls of the strut. In one embodiment, the thickness of the coating is about 1 to 100 microns. In an exemplary embodiment, the thickness of the coating can be at any range between about 5 and 20 microns. In an exemplary embodiment, the thickness of the coating can be, for example, about 5, about 10, about 15, or about 20 microns.

In some embodiments, the coating is a pure drug or therapeutic substance layer. In some embodiments, the coating is a combination of more than one drug or therapeutic substance without any polymers. In some embodiments the coating can be a combination of at least one polymer and at least one drug or therapeutic substance. Combination is defined as blending, mixing, dispersing, conjugating, and/or bonding of the drug/therapeutic substance to the polymer. The coating polymer can be the same as or different than a polymer from which the stent is made. At least one of the polymers for the coating can be the same or different than at least one of the polymers of the stent structure.

In some embodiments, the coating can include a primer layer and/or a topcoat layers or sub-layers. The primer layer will be beneath the drug/therapeutic substance layer and the topcoat layer above it. Both the primer layer and the topcoat layer can be without any drugs/therapeutic substances. In some embodiments, some drug may incidentally migrate into the primer layer or region. The topcoat layer reduces the rate of release of the drug and/or provides for biobeneficial properties.

The thin coating can be deposited by spray application, electrostatic application, "ink-jet"-type application, plasma deposition and the like. These processes are known in the art. A coating composition including polymer(s), solvent(s), and optionally drug(s)/therapeutic substance(s) can be used, for example. In some embodiments, the amount of solvent included in the composition can be low so as to allow for formation of the thin coating. In some embodiments, the method of coating may include modifying at least one process parameter of the spraying so that a weight percent of solvent in coating material applied on the polymeric surface is less than about 30 wt %, 20 wt %, 15 wt %, or more narrowly, 10 wt %.

The stent or the coating can be made from a material including, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanrhydride, poly(glycolic acid), poly(glycQlide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating the stent include ethylene vinyl alcohol copolymer (commonly known by the generic name EVOH or by the trade name EVAL), poly(butyl methacrylate), poly(vinylidene fluoride-co-hexafluorororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The stent can also be made from the following metallic materials or alloys: cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The coating can be made from the following materials: poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the substrate coating described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

In some embodiments, the coating preferably includes a fluoropolymer such as a Solef™ polymer (e.g., PVDF-HFP).

In some embodiments, the coating can be made from or further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Dosages

On-device dosages of at least one pharmaceutically active agent or agents may be determined by means known in the art. Typically, the dosage is dependent upon the particular drug employed and medical condition being treated to achieve a therapeutic result. In one embodiment, the amount of drug represents about 0.001 percent to about seventy percent of the total coating weight, or about 0.01 percent to about sixty percent of the total coating weight. In one embodiment, the weight percent of the therapeutic agents in the carrier or polymer coating is 1% to 50%, 2% to 45, 5% to 40, or 10 to 35%. In another embodiment, it is possible that the drug may represent as little as 0.0001 percent to the total coating weight. In another embodiment, the amount of selected drugs loaded onto a 16 mm long stent range from about 30 to about 105 micrograms per coating layer.

In an exemplary embodiment, the dosage or concentration of, e.g., resveratrol and/or quercetin based on surface area on a typical coronary stent and/or other medical device can range from about 0.1 to about 5 $\mu g/mm^2$, or more than about 0.7 $\mu g/mm^2$ (at lower dosage restenosis rates are higher), or less than about 3.0 µg/mm² (higher will be cytotoxic), or ranging from 1.0 and 1.8 µg/mm², and or about 1.4 µg/mm². In an exemplary embodiment, the dosage or concentration of, e.g., resveratrol and/or quercetin based on surface area on a typical coronary stent and/or other medical device can range from about 0.5 µg/mm² to about 35 µg/mm². In an exemplary embodiment, the dosage or concentration of, e.g., resveratrol and/or quercetin based on surface area on a typical coronary stent and/or other medical device can range from about 1 µg/mm² to about 100 µg/mm². In an exemplary embodiment, the dosage or concentration of, e.g., resveratrol and/or quercetin based on surface area on a typical coronary stent and/or other medical device can range from about 1 µg/mm² to about 2 µg/mm². In an exemplary embodiment, the dosage or concentration of, e.g., resveratrol and/or quercetin based on surface area on a typical coronary stent and/or other medical device can range from about 1 µg/mm² to about 5 µg/mm². In an exemplary embodiment, for a typical series of coronary stent varying in length from 8.00 to 39.00 mm, the total resveratrol and/or quercetin content will vary from 50 µg to 250 µg. Suitable dosaging for drug-eluting stents is further described in U.S. Pat. No. 6,908,622, the disclosure of which is incorporated herein by reference.

The dosage or concentration of e.g. resveratrol and/or quercetin based on surface area on a typical coronary stent may be is 0.1 and 5 µg/mm² In another embodiment, the dosage is more than about 0.7 µg/mm² (at lower dosage restenosis rates are higher) and less than about 3.0 µg/mm², such as ranging from 1.0 and 1.8 µg/mm², e.g., about 1.4 µg/mm². Typically, the amount of resveratrol and/or quercetin will increase linearly with the length of the stent. For example, for a typical series of coronary stent varying in length from 8.00 to 39.00 mm, the total resveratrol and/or quercetin content will vary from 50 µg to 250 µg.

The dosage or concentration of a flavonoid or derivative thereof based on surface area on a stent (e.g. a typical coronal stent) may be is 0.1 and 40 µg/mm². In one embodiment, the dosage of a flavonoid or derivative thereof based on surface area of a device of the invention is more than about 0.2., 0.5, 1.0, 2.0, 5.0 or 10 µg/mm². In another embodiment, the dosage of a flavonoid or derivative thereof based on surface area of a device of the invention is less than about 30.0, 20.0, 15.0, 10.0, 5.0, 3.0 or 2.0 µg/mm². Generally, the amount of the flavonoid or derivative thereof will increase linearly with the length of the stent. For example, for a typical series of coronary stent varying in length from 8.00 to 39.00 mm, the total flavonoid (or derivative thereof) content will vary from 28 µg to 3500 µg.

Method of Treatment

In one embodiment, the implantable devices disclosed herein are implanted in a subject in need thereof to achieve a therapeutic effect, e.g., therapeutic treatment and/or prophylactic/preventative measures. Those in need of treatment may include individuals already having a particular medical disease as well as those at risk for the disease (e.g., those who are likely to ultimately acquire the disorder). A therapeutic method can also result in the prevention or amelioration of symptoms, or an otherwise desired biological outcome, and may be evaluated by improved clinical signs, delayed onset of disease, reduced/elevated levels of lymphocytes and/or antibodies.

In one embodiment, the method is used for treating at least one disease or condition associated with vascular injury or angioplasty. Angioplasty may be performed as part of "revascularization" treatment for "artherosclerosis," which as used herein means diseases in which plaque, made up of cholesterol, fats, calcium, and scar tissue, builds up in the wall of blood vessels, narrowing the lumen and interfering with blood flow. "Revascularization," as used herein means any treatment that re-establishes brisk blood flow through a narrowed artery, including bypass surgery, angioplasty, stenting, and other interventional procedures. Secondary complications following revascularization may include restenosis, neointima, neointimal hyperplasia and thrombosis. "Restenosis," as used herein is defined as the re-narrowing of an artery in the same location of a previous treatment; clinical restenosis is the manifestation of an ischemic event, usually in the form of recurrent angina. "Neointima," as used herein is defined as the scar tissue made up of cells and cell secretions that often forms as a result of vessel injury following angioplasty or stent placement as part of the natural healing process. "Neointimal hyperplasia," as used herein means excessive growth of smooth muscle cells from the inner lining of the artery. After angioplasty and/or stenting, excessive growth of these cells can narrow the artery again. "Thrombosis," as used herein means the formation of a blood clot within a blood vessel or the heart cavity itself and a "thrombus" is a blood clot.

Three pathophysiological phases can be distinguished subsequent to revascularization. Stage I, the thrombotic phase (days 0-3 after revascularization). This stage consists of rapid thrombus formation. The initial response to arterial injury is explosive activation, adhesion, aggregation, and platelet deposition. The platelet thrombus may frequently be large and can grow large enough to occlude the vessel, as occurs in myocardial infarction. Within 24 hours, fibrin-rich thrombus accumulates around the platelet site. Two morphologic features are prominent: 1) platelet/fibrin, and 2) fibrin/red cell thrombus. The platelets are densely clumped at the injury site, with the fibrin/red cell thrombus attached to the platelet mass.

Stage II, the recruitment phase (days 3-8). The thrombus at arterial injury sites develops an endothelial cell layer. Shortly after the endothelial cells appear, an intense cellular infiltration occurs. The infiltration is principally monocytes that become macrophages as they leave the bloodstream and migrate into the subendothelial mural thrombus. Lymphocytes also are present, and both types of cells demarginate from the bloodstream. This infiltrate develops from the luminal side of the injured artery, and the cells migrate progressively deeper into the mural thrombus.

Stage III, the proliferative phase: (day 8 to final healing). Actin-positive cells colonize the residual thrombus from the lumen, forming a "cap" across the top of the mural thrombus in this final stage. The cells progressively proliferate toward the injured media, resorbing thrombus until it is completely gone and replaced by neointimal cells. At this time the healing is complete. In the pig this process requires 21-40 days, depending on residual thrombus thickness. Smooth muscle cell migration and proliferation into the degenerated thrombus increases neointimal volume, appearing greater than that of thrombus alone. The smooth muscle cells migrate from sites distant to the injury location, and the resorbing thrombus becomes a bioabsorbable "proliferation matrix" for neointimal cells to migrate and replicate. The thrombus is colonized at progressively deeper levels until neointimal healing is complete.

In one embodiment, the method of the invention can be used to treat these conditions subsequent to revascularization, such as those conditions subsequent to any of the three stages described above, e.g., activation, adhesion, aggregation, platelet deposition, thrombosis, platelet aggregation, proliferation, and neointima.

In one embodiment, the active agent and/or agents are for the prevention or treatment of restenosis subsequent to angioplasty, such as the inhibition of neointimal hyperplasia subsequent to angioplasty.

In one embodiment, the methods of the invention are directed to the prevention of acute, subacute and chronic secondary complications associated with angioplasty. Such secondary complications subsequent to and/or associated with angioplasty are defined herein above and include, e.g., restenosis, neointima, neointimal hyperplasia, thrombosis and inflammation.

In one embodiment, the methods disclosed herein are directed to treating undesired cell proliferation, which is often a component of many disease processes. Undesired cell growth can be a component of restenosis, the recurrence of stenosis or artery stricture after corrective surgery. Restenosis occurs after coronary artery bypass (CAB), endarterectomy, heart transplantation, or after angioplasty, atherectomy, laser ablation or stenting. Restenosis is the result of injury to the blood vessel wall during the lumen opening procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat angioplasty or other procedure to alleviate the restenosis.

The therapeutic compounds disclosed herein will be delivered locally to reduce side effects from high dose systemic delivery. The local delivery options can include release from a drug eluting stent, delivery by a drug eluting balloon or local delivery/activation by remote techniques. The latter could include systemic delivery of nanocomposite particles into the circulation coupled by remote capture or release of the therapeutic agents by acoustic, electrical, magnetic or optical energy sources. (e.g., carotid or other peripheral vesselendarterectomy, vascular bypass, stent or prosthetic graft procedure). For example, a coated stent or device as disclosed herein may be implanted at the vascular site of interest for controlled release of the pharmaceutically active agents over a desired time period.

Method of Making a Coated Drug Eluting Stent or Balloon Catheter

The practice of coating implantable medical devices with a synthetic or biological active or inactive agent is known. Numerous processes have been proposed for the application of such a coating. Soaking or dipping the implantable device in a bath of liquid medication is suggested by U.S. Pat. No. 5,922,393 to Jayaraman, soaking in an agitated bath, U.S. Pat. No. 6,129,658 to Delfino et al. Devices introducing heat and/or ultrasonic energy in conjunction with the medicated bath are disclosed in U.S. Pat. No. 5,891,507 to Jayaraman and U.S. Pat. No. 6,245,104 to Alt. The device of U.S. Pat. No. 6,214,115 to Taylor et al. suggests spraying the medication by way of pressurized nozzles, see U.S. Patent Application No. 2006/0156976 (Shekalim).

Initially such coatings were applied at the time of manufacture. Wrapping the implantable device with medicated conformal film is disclosed in U.S. Pat. No. 6,309,380 B1 to Larson et al. Dipping or soaking in a medicated bath just prior to implantation are suggested in U.S. Pat. No. 5,871,436 to Eury, U.S. Pat. No. 6,730,120 to Berg et al., and U.S. Pat. No. 6,1171,232 to Papandreou et al. U.S. Pat. No. 6,395,326 B1 to Wu provides a bathing chamber for use with specific implantable device such as the stent deployed on the balloon of a catheter.

Each of the methods and devices intended for use just prior to implantation, listed above, deposit the coating material onto any and all surfaces that are exposed to the coating. This may result in depositing coating material on surfaces on which the coating is unwanted or undesirable. Further, the coating may crack or break away when the implantable is removed from the implantation apparatus. An example of this would be a stent deployed on a catheter balloon. As the balloon is inflated and the stent is expanded into position, the coating may crack along the interface between the stent and the balloon. These cracks may lead to a breaking away of a portion of the coating from the stent itself. Similar problems can occur in cases where the coating technique fails to prevent inadvertent overlapping with the edges (e.g., internal surfaces along the edges) of various devices (e.g., struts of stents). This, in turn, may affect the medicinal effectiveness of the coating, and negatively affect the entire medical procedure.

It is known to use Ink-Jet technology to apply a liquid to selected portion of a surface. In the paper "Applications of Ink-Jet Printing Technology to BioMEMS and Microfluidic Systems," presented at the SPIC Conference on Microfluidics and BioMEMS, October, 1, the authors, Patrick Cooley, David Wallace, and Bogdan Antohe provide a fairly detailed description of Ink-Jet technology and the range of its medically related applications.

The present invention incorporates at least one compound coated onto a vascular stent and/or other medical device. For a detailed description of such a stent and/or other medical device and how it may be coated, please see U.S. Pat. No. 7,247,338, to David Y. H. Pui and Da-Ren Chen, titled "Coating medical devices", which is herein incorporated by reference in its entirety. For other examples of how such a stent may be coated, please see U.S. Pat. No. 6,093,557, to David Y. H. Pui and Da-Ren Chen, titled "Electrospraying apparatus and method for introducing material into cells," U.S. Pat. No. 6,399,362 to David Y. H. Pui and Da-Ren Chen, titled "Electrospraying apparatus and method for introducing material into cells," U.S. Pat. No. 6,746,869 to David Y. H. Pui and Da-Ren Chen, titled "Electrospraying Apparatus and Method for Coating Particles," and U.S. Pat. No. 6,764,720, to David Y. H. Pui and Da-Ren Chen, titled "High mass throughput particle generation using multiple nozzle spraying" which are herein incorporated by reference in their entirety.

Preferably the method of making a coated stent according to the present invention incorporates a ElectroNanospray™ process for creating the coating because of its uniformity of drug coverage, even coating, and lack of pooling and webbing. Additionally, its use of a dual capillary co-axial nozzle allows for the delivery of multiple agents, as is included in this invention. However, the present invention is not limited to this technology for coating. Another technology, which is not limiting, that could be used is the presence of multiple polymers for support.

All coating processes are to be optimized according to the present invention for variables including the photosensitivity of resveratrol and quercetin, the levels of resveratrol required for eliciting efficacious results, synergistic effects between the two drugs that result in differing levels of drug loading, and necessary processing steps to decrease or eliminate the possible oxidation of said compounds.

The invention will be illustrated in more detail with reference to the following Examples, but it should be understood that the present invention is not deemed to be limited thereto.

EXAMPLES

Example 1

Determining whether quercetin potentiates the vascular protective effects of resveratrol in vivo, utilizing a mouse carotid artery injury model. Female B6.129 mice were administered a high fat diet, in some cases mixed together with 50 mg/kg resveratrol (RESV), 10 mg/kg quercetin (QUER), or resveratrol plus quercetin, for 2 weeks. The carotid artery injury procedure was conducted and the animals were fed the high fat diet plus polyphenols for an additional two weeks. The animals were then sacrificed, and the carotid arteries were excised and assessed for neointimal areas. The results indicate that oral treatment with resveratrol dramatically reduced neointimal area. Though treatment with quercetin alone exhibited no significant effect, it potentiated the effects of resveratrol when the two polyphenols were administered in combination.

Example 2

Figure 10:
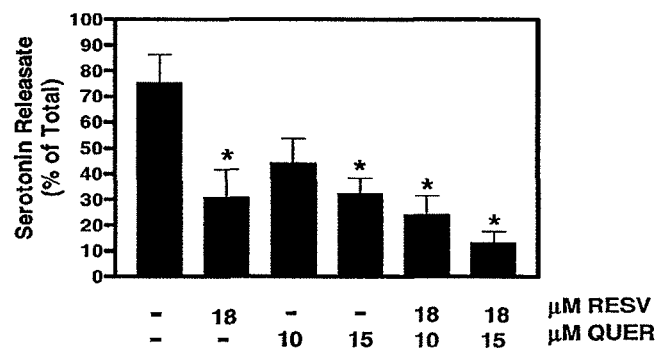
FIG. 10 is a bar chart showing the release of tritiated serotonin from platelets incubated for 3 h with resveratrol or quercetin and then activated with 5 µM ADP. Values represent means+/−standard error. ANOVA revealed a significant effect of treatment. *Denotes significance compared to vehicle.

Effects of resveratrol/quercetin combination on platelet activation. Prior reports suggest the efficacy of quercetin, and to some extent, resveratrol, in reducing platelet activation and aggregation. Thus, the addition of quercetin to the drug eluting stent should make the described invention preferable to current generation DES and/or other medical devices that have the undesired side effect of thrombogenesis. To determine the efficacy of these compounds in reducing platelet activation, platelets isolated from healthy, male donors were incubated with resveratrol, quercetin, or resveratrol plus quercetin. The doses were selected based on prior studies. In experiments examining effects on VSMC proliferation, resveratrol's $EC_{50}$ for inhibiting DNA synthesis was 18 µM, while its $EC_{50}$ for reducing numbers of cells was 25 µM. Cells were treated with the lower dose, 18 µM resveratrol, and added to this 10 and 15 µM quercetin, doses about half its reported $EC_{50}$ for reducing VSMC proliferation. Doses of each that were slightly below their maximal effective doses were utilized, so as to be able to discern the additive or synergistic effects of the drugs. The polyphenol treatments exhibited dramatic effects on platelet activation. Treatment with 18 µM resveratrol reduced serotonin release by ~60%, and incubation with 10-15 µM quercetin reduced serotonin release by 40-50% (FIG. 10). Cotreatment with 18 µM resveratrol plus 10 µM quercetin reduced the activation by 65% compared to controls, and cotreatment with 15 µM quercetin reduced activation by 80%. Thus, these experiments demonstrate that quercetin potentiated the effects of resveratrol on platelet activation.

Example 3

Figure 11:
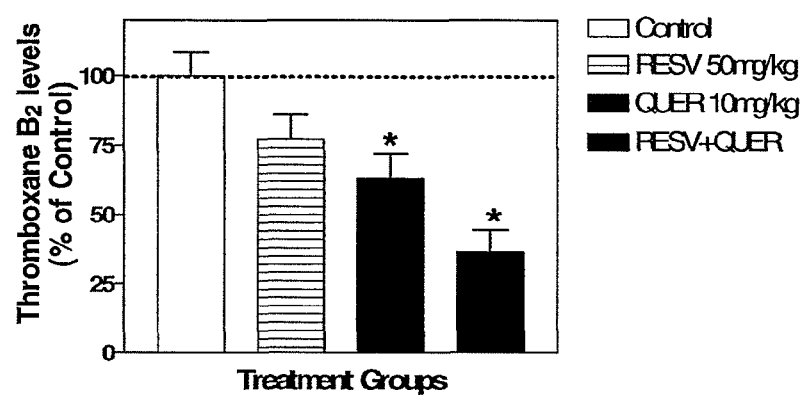
FIG. 11 is a bar chart showing the effects of 4 weeks oral administration of 50 mg/kg resveratrol, 10 mg/kg quercetin or resveratrol+quercetin on serum thromboxane B2 levels in B6.129 mice subjected to the carotid artery injury procedure. One-way ANOVA revealed a significant effect of treatment. *Denotes a significant change compared to control mice.

In vivo experiments determining the efficacy of combined treatment with resveratrol/quercetin in reducing platelet activation. To confirm the in vitro experiments in an in vivo rodent model, the effects of oral administration of 50 mg/kg resveratrol were compared to treatment with resveratrol plus 10 mg/kg quercetin in the mouse carotid artery injury model. Plasma levels of thromboxane $B_2$ ($TBX_2$), a known marker for platelet activation, were assessed. Though resveratrol treatment alone had no significant effect on plasma $TXB_2$ levels (FIG. 11), treatment with quercetin alone reduced $TXB_2$ levels by 40%, and treatment with quercetin plus resveratrol reduced $TXB_2$ by 70%. Thus, treatment with a resveratrol/quercetin combination induces additive and synergistic effects on platelet activation in vivo.

Example 4

Figure 12:
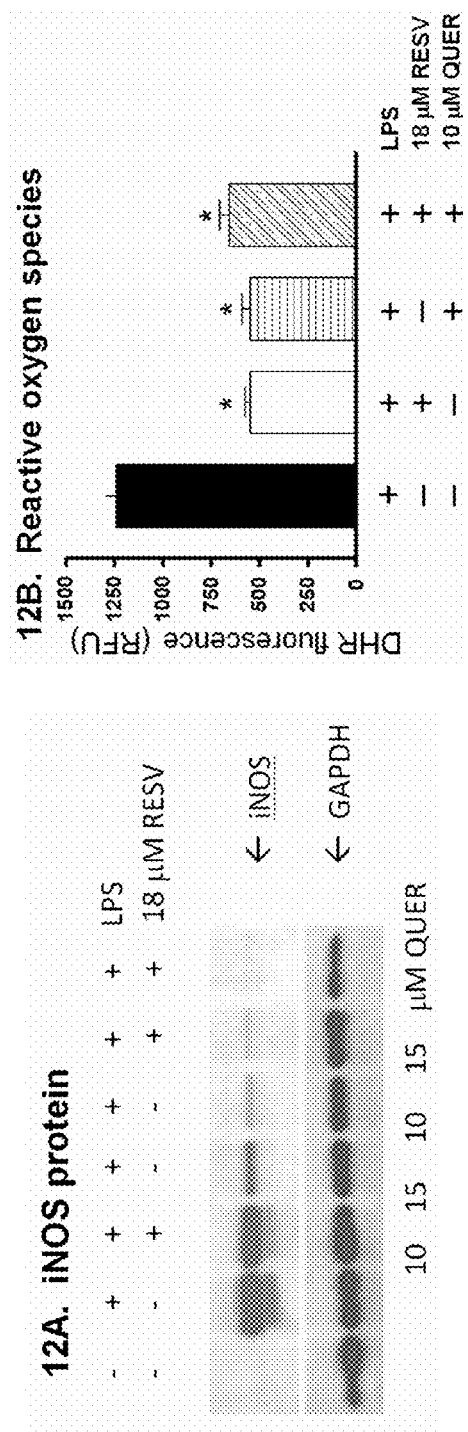
FIG. 12 shows the effects of resveratrol and quercetin on LPS-induced activation of macrophages, as indicated by increases in iNOS protein (FIG. 12A) and reactive oxygen species (FIG. 12B). ANOVA revealed a significant effect of treatment. *Indicates differences compared to LPS alone.

Effects of resveratrol/quercetin combination on the activation of inflammatory cells. Resveratrol is well-known to inhibit inflammatory responses via inhibition of NFκB activation. To test the efficacy of a resveratrol/quercetin combination in inhibiting the activation of macrophages, effects of polyphenol treatments either alone or in combination with quercetin were assessed in cultures of lipopolysaccharide (LPS) stimulated macrophages. Macrophage activation was determined by increases in protein levels of inducible nitric oxide synthase (iNOS) and by levels of reactive oxygen species (ROS). Treatment with 18 µM resveratrol reduced iNOS protein levels by ~25%, in agreement with prior reports documenting the anti-inflammatory activity of resveratrol (FIG. 12). However, quercetin more potently diminished macrophage activation, reducing iNOS protein by ~75 and 90% at 10 and 15 µM, respectively. In addition, the combination of 18 µM resveratrol plus 10-15 µM quercetin virtually abolished all macrophage activation. The data for ROS production were similar. This compilation of data thus demonstrates the efficacy of the drug combination in inhibiting the activation of inflammatory cells.

Example 5

Figure 13:
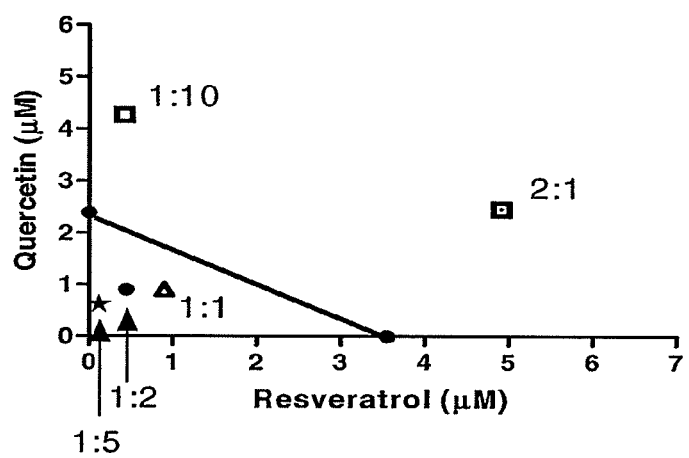
FIG. 13 is an isobologram for predicting the synergistic effects of a resveratrol/quercetin combination on macrophage activation. Macrophages were incubated with differing dose ratios of resveratrol:quercetin and were stimulated with LPS. Activation was assessed as increases in nitric oxide release. The $IC_{50}$'s for each dose ratio were calculated using CaluSyn software and were used to plot the isobologram. The line depicted above indicates the point at which additive responses are observed ($C_1$=1). Points lying above the line indicate antagonism, whereas points below the line represent synergism.

Isobolograms for the determination of synergistic dose ratios for a resveratrol/quercetin combination. To determine the dose ratios for achieving maximal synergistic effects, activation in LPS-stimulated cells macrophages incubated with constant dose ratios of resveratrol and quercetin was measured. The $IC_{50}$ for each dose ratio was calculated using CalcuSyn software, and these concentrations were used to construct an isobologram (FIG. 13). Dose ratios exhibiting synergism were 1:5, 1:2, and 1:1 resveratrol:quercetin. These dose ratios exhibited combination indices (CI values) of ~0.5. Briefly, CI=1 denotes additive effects, CI>1 denotes antagonism, and CI<1 indicates synergism. As an example of the synergistic effects of the resveratrol/quercetin combination, the $IC_{50}$'s for individual treatments of resveratrol and quercetin were 3.5 and 2.4 µM, respectively. However, when the drugs were administered at a 1:1 dose ratio, 50% inhibition could be achieved at 0.9 µM concentrations of each compound.

Example 6

Development of drug eluting stent models for in vitro analysis of efficacy. For the purposes of modeling DES release and biocompatibility in an inexpensive in vitro system, stainless steel flat surfaces coated with drug-containing polymer were utilized. The bare metal flats (0.2"×0.3") were coated with a polyisobutylene-polystyrene triblock copolymers containing the active agents with two distinct surface morphologies—smooth and nanoparticulate (high surface area) matrices. The ElectroNanospray™ process for depositing drug-containing nanoparticles, typically 50-300 nm in diameter, was utilized so as to achieve uniformity of drug coverage, even coating, and lack of pooling. Differences in coating morphologies can culminate in differences in drug release characteristics. Initial biocompatibility testing on both conformations was conducted. Each coating type was loaded with two concentrations of either resveratrol or quercetin.

Figure 14:
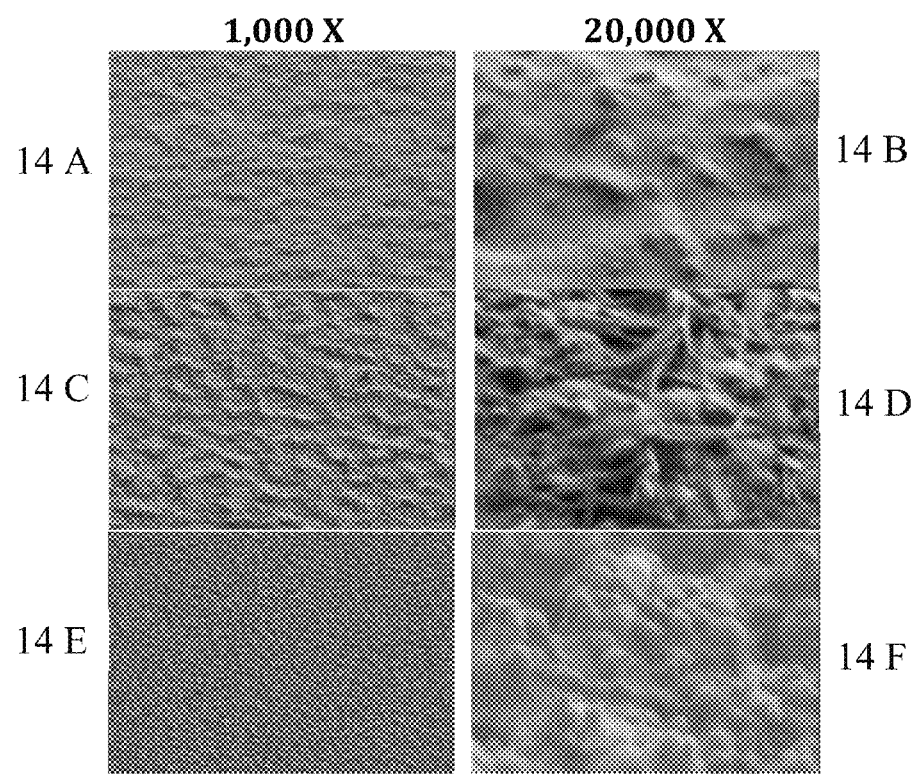
FIG. 14 is a scanning electron microscopy images at 1,000× (left.

The coating process needs to be able to minimize variation so that each flat, and eventually each stent, releases the target amount of drug at a desired rate. FIG. 14 illustrates scanning electron microscopy (SEM) images of drug-containing polymer applied using the ElectroNanospray™ process. FIG. 14 furthermore compares polyisobutylene-polystyrene triblock copolymer surfaces of both open and closed morphologies containing resveratrol and quercetin nanoparticles. These images display a uniform coating with either smooth (closed) or rough (open) surfaces.

Example 7

Figure 15:
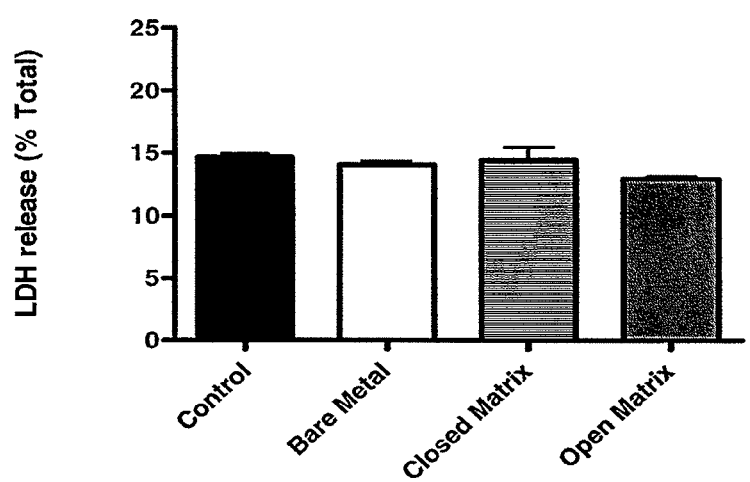
FIG. 15 is a bar chart showing the Lactate Dehydrogenase (LDH) cytotoxicity assay from the 48-hour endpoint experiment expressed as amount released in medium over total LDH.

Biocompatibility is an important concern when developing an implantable therapeutic. In order to assess cytotoxicity of the polymer, the bare metal flats or flats coated with polymer only were incubated with vascular smooth muscle cells (VSMC) for 48 hours. During the experiment, the flats were separated from the cells using a 0.4 µm semi-permeable transwell insert. To assess cytotoxicity, medium collected after this incubation was assayed for lactate dehydrogenase (LDH), a known marker for cytotoxicity, as LDH is released from the cell when it becomes injured or "leaky." Neither bare metal flats nor flats coated with polyisobutylene-polystyrene triblock copolymer of either morphology had any effect on LDH release compared to VSMC incubated without flats (FIG. 15). Thus, this preliminary experiment suggests that the polymer-coated flats exhibit no cytoxicity to VSMC.

Figure 16:
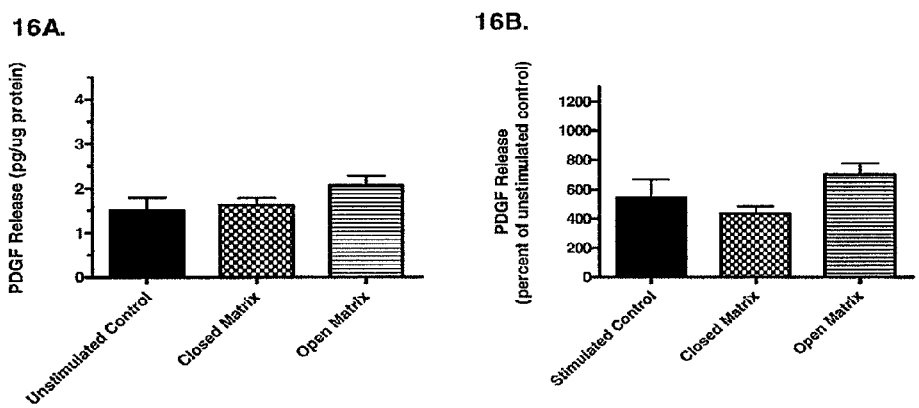
FIG. 16 is a set of bar charts showing the effects of arbIBS-coated flats on platelet activation. Bare metal flats coated using a closed or an open morphology of arbIBS polymer were incubated in Tyrode's buffer for 48 h at 37° C. Platelets were isolated and incubated for 1 h with the resulting conditioned Tyrode's buffer. Basal levels of activation (FIG. 16A), compared to ADP-stimulated platelet activation (FIG. 16B), were assessed by enzyme-linked immunosorbent assay for release of platelet-derived growth factor (PDGF) into the medium. Data are expressed as means+/−standard error. No significant effects of the polymer-coated flats were detected for levels of either basal or ADP-stimulated activation.

While platelet activation is also an important factor in restenosis, polymers that promote platelet activation would likewise be undesirable for use in a drug eluting stent. To test the effects of the polymer-coated flats on platelet activation, bare metal flats coated with polyisobutylene-polystyrene triblock copolymer using a closed compared to an open morphology were incubated for 48 h in medium. Platelets were then isolated from healthy, male donors and were incubated with the resulting conditioned medium. Platelet activation was assessed as platelet-derived growth factor (PDGF) release in either a basal (FIG. 16a) or ADP-stimulated (FIG. 16b) condition. Results indicated no significant effects of the polyisobutylene-polystyrene triblock copolymer coated flats of either morphology.

Example 8

Figure 17:
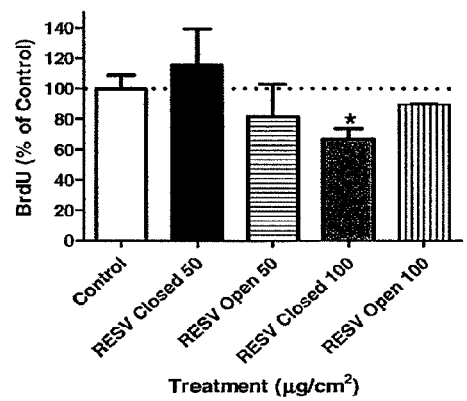
FIG. 17 is a set of bar charts showing the efficacy of drug-eluting flats on inhibition of VSMC proliferation. Bare metal flats coated with resveratrol—(FIG. 17A) or quercetin—(FIG. 17B) containing arbIBS of either a closed or an open morphology were incubated in semi-permeable transwell inserts in plates containing VSMC. The bromodeoxyuridine (BrdU) incorporation assay for cell proliferation was conducted after 48 h of drug elution. The data are expressed as percent of control (wells not containing flats). *Denotes significance compared to controls.
Figure 17:
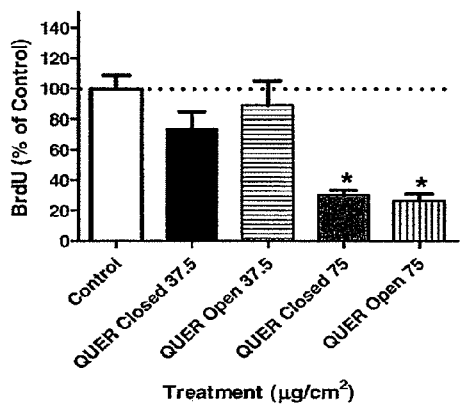

Another major goal in the development of a drug-eluting polymer is to ensure that the system can release an adequate amount of drug to inhibit local smooth muscle cell proliferation. The polyisobutylene-polystyrene triblock copolymers coated flats containing resveratrol or quercetin were incubated in semi-permeable transwell inserts in plates containing VSMC. After 48 hours of drug elution, resveratrol coated in a smooth (closed) matrix polyisobutylene-polystyrene triblock copolymer significantly inhibited proliferation at the 100 µg/cm² loading concentration. Quercetin significantly inhibited proliferation in flats coated at 75 µg/cm², in either the particulate (open) or the smooth (closed) polyisobutylene-polystyrene triblock copolymer matrices. Data supporting these results are shown in FIG. 17.

Figure 18:
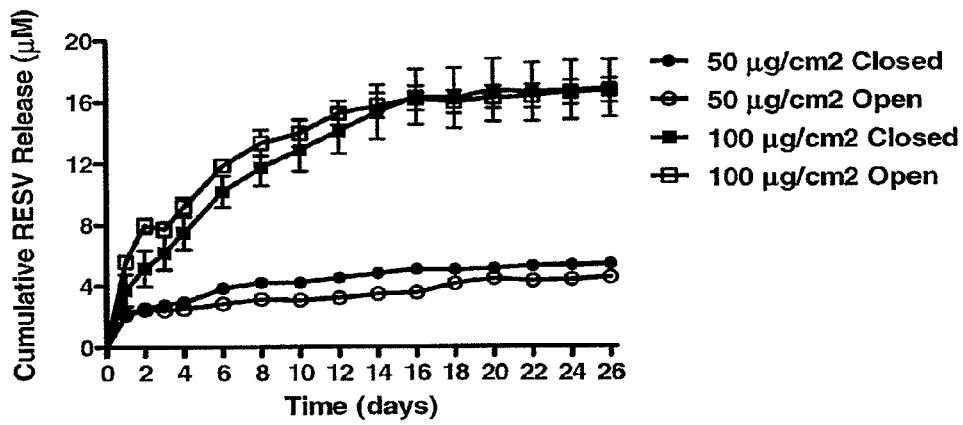
FIG. 18 shows the release of resveratrol from smooth (closed) versus particulate (open) matrix arbIBS polymer-coated bare metal flats. Polymer coated flats were incubated in medium at 37° C. for 28 d. Resveratrol concentration in the medium was assessed at 2 d intervals using high performance liquid chromatography. The data are expressed as means+/−standard error for cumulative release in micromolar concentrations (FIG. 18A) compared to a percent of total drug loaded (FIG. 18B).
Figure 18:
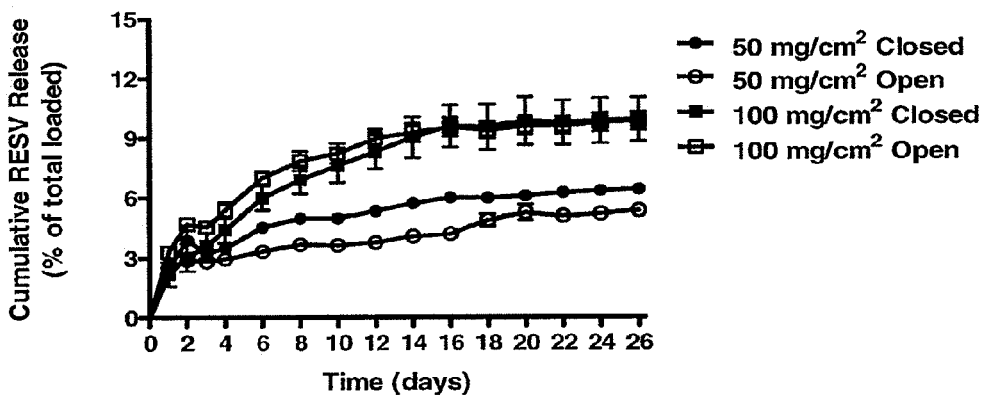

Determination of resveratrol release was performed using reversed phase high performance liquid chromatography (HPLC) coupled to a 4-channel Coularray electrochemical detector run at 590, 660, 730, and 800 mV. Results indicate that resveratrol release from the 100 mg/cm² coated flat was approximately 4-fold greater than from the 50 mg/cm²-coated flat, regardless of the morphology (FIG. 18). Slight, though insignificant effects of the morphology on drug release were observed, with the closed matrix trending toward a greater release profile compared to the open matrix. Importantly, the flats eluted low micromolar concentrations of resveratrol that are in a range that exhibits efficacy in our in vitro tests. Also important is that at 28 days, only 5-10% of the total drug loaded onto the flats had eluted, suggesting that in stents coating in a similar manner, sufficient drug should remain in the coating to achieve efficacy over several months after stent placement. Polymer deposition via the ElectroNanospray™ process creates a textured surface with no noticeable defects or voids. This texture provides high surface area for the biostable polymer to be in contact with the surrounding environment. This is important because exposure to new drug-containing polymer through degradation does not occur in this system as it would with biodegradable polymers. Cytotoxicity and proliferation data on the polymer-only samples provide evidence that the polyisobutylene-polystyrene triblock copolymer is biocompatible. Establishing biocompatibility is a critical step in the development of the stent models. Proliferation data from drug-containing polyisobutylene-polystyrene triblock copolymer (FIG. 17) suggests that quercetin is releasing faster than resveratrol from the polymer within the first 48 hours.

While the invention has been described in detail and with reference to specific examples thereof, it will be apparent to one skilled in the art that various changes and modifications can be made therein without departing from the spirit and scope thereof.

What is claimed is:

1. A drug eluting intravascular stent comprising:
   (a) a generally cylindrical stent body;
   (b) an adherent layer on the stent comprising a composite of polymer and a first active agent selected from a group consisting of resveratrol, pharmaceutically acceptable salts thereof, and pharmaceutically acceptable derivatives thereof, and a second active agent selected from a group consisting of quercetin, pharmaceutically acceptable salts thereof, and pharmaceutically acceptable derivatives thereof, wherein said first and second active agents are dispersed within the polymer,
   wherein the concentration of the first active agent based on a surface area of the stent ranges from about 1 to about 5 µg/mm², and the concentration of the second active agent based on the surface area of the stent ranges from about 1 to about 5 µg/mm²,
   and wherein the composite includes a plurality of layers.

2. A stent according to claim 1, wherein the stent body has a metal surface.

3. A stent according to claim 1, wherein the stent body is micro- or nanoporous.

4. A stent according to claim 1, wherein the stent body has a polymeric surface.

5. A stent according to claim 1, wherein the polymer is a bioabsorbable polymer.

6. A stent according to claim 1, wherein the polymer is a biostable polymer.

7. A stent according to claim 1, wherein a weight of the first active agent and a weight of the second active agent are in a ratio which is selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1.

8. The stent according to claim 1, wherein a weight of the first active agent and a weight of the second active agent are in a ratio which is selected from a group consisting of about 1:5, about 1:2, and about 1:1.

9. The stent of claim 1 wherein the coating is a polymer selected from a group consisting of polystyrene-polyisobutylene block copolymers, polyethylene terephthalate, poly(lactide), poly(lactide-co-glycolide), poly(caprolactone), poly(lactide-co-caprolactone), poly-(hydroxybutyrate/hydroxyvalerate) copolymer, poly(vinylpyrrolidone), polytetrafluoroethylene, poly(2-hydroxyethylmethacrylate), poly(n-butyl methacrylate), poly(ethylene-co-vinyl acetate), poly(vinylidene fluoride-co-hexafluoropropene), poly (etherurethane urea), silicones, acrylics, epoxides, polyesters, polyurethanes, desaminotyrosine polyarylate, parylenes [polyxylylenes], polyphosphazene polymers, fluoropolymers, polyamides, isoolefin homopolymers and copolymers, vinyl homopolymers and copolymers, acrylate homopolymers and copolymers, methacrylate homopolymers and copolymers, polyethers, polyesters, polycarbonates and copolymers, polyethylene oxides, poly(ethylene glycol) and derivatives, carbo-films, self-assembling polymer films and liposomes cellulosics, chondroitin-sulfate, gelatin, amino acid-based polymers, fibrin, chitin, extracellular matrix proteins, heparinized coatings, phospholipid liposomes and self-assembled arrays, poly-lactides and mixtures thereof.

10. A stent according to claim 1 wherein
a first weight comprises a combined weight of the first and second active agents;
a second weight comprises a weight of the polymer; and
the first weight and the second weight are in a ratio selected from a group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1.

11. The stent according to claim 10, wherein the ratio is varied in some of the layers.

12. The stent of claim 1 wherein at least one of the active agents are selected from agents which treat or prevent atherosclerosis, stenosis, restenosis, smooth muscle cell proliferation, platelet cell activation and other clotting mechanisms, occlusive disease, or other abnormal lumenal cellular proliferation condition within a body of a patient.

13. The stent of claim 1, wherein each of the active agents have release profiles selected from a group consisting of a same release profile and a different release profile.

14. The stent of claim 1, wherein the active agents have a release profile which is selected from a group consisting of a rapid release profile and a delayed release profile.

15. The stent of claim 1, wherein a rapid profile coating releases one of the active agents substantially within one to a few hours.

16. The stent of claim 1, wherein a delayed profile coating releases one of the active agents over a period of at least one month, at least two months, at least six months, or at least one year.

* * * * *